United States Patent
Sholev

(10) Patent No.: US 10,149,730 B2
(45) Date of Patent: Dec. 11, 2018

(54) CONTROL UNIT FOR A MEDICAL DEVICE

(71) Applicant: Human Extensions Ltd., Netanya (IL)

(72) Inventor: Mordehai Sholev, Moshav Amikam (IL)

(73) Assignee: Human Extensions Ltd., Netanya (IL)

( * ) Notice: Subject to any disclaimer, the term of this patent is extended or adjusted under 35 U.S.C. 154(b) by 81 days.

(21) Appl. No.: 14/911,467

(22) PCT Filed: Sep. 1, 2014

(86) PCT No.: PCT/IL2014/050781
§ 371 (c)(1),
(2) Date: Feb. 11, 2016

(87) PCT Pub. No.: WO2015/029041
PCT Pub. Date: Mar. 5, 2015

(65) Prior Publication Data
US 2016/0184040 A1    Jun. 30, 2016

Related U.S. Application Data

(60) Provisional application No. 61/972,528, filed on Mar. 31, 2014, provisional application No. 61/872,727, filed on Sep. 1, 2013.

(51) Int. Cl.
| | | |
|---|---|---|
| G05G 11/00 | (2006.01) | |
| A61B 34/00 | (2016.01) | |
| A61B 17/29 | (2006.01) | |
| A61B 17/00 | (2006.01) | |

(52) U.S. Cl.
CPC ........ *A61B 34/71* (2016.02); *A61B 17/00234* (2013.01); *A61B 17/2909* (2013.01); *A61B 2017/00424* (2013.01); *A61B 2017/2923* (2013.01); *A61B 2017/2925* (2013.01)

(58) Field of Classification Search
CPC ...... A61B 17/2902; A61B 2017/00353; A61B 2017/00017
See application file for complete search history.

(56) References Cited

U.S. PATENT DOCUMENTS

| | | |
|---|---|---|
| 5,599,151 A | 2/1997 | Daum et al. |
| 2003/0109857 A1 | 6/2003 | Sanchez et al. |
| 2005/0187575 A1 | 8/2005 | Hallbeck et al. |
| 2008/0065116 A1 | 3/2008 | Lee et al. |
| 2011/0112517 A1 | 5/2011 | Peine et al. |
| 2011/0118748 A1 | 5/2011 | Itkowitz |
| 2012/0004502 A1 | 1/2012 | Weitzner et al. |
| 2012/0095298 A1 | 4/2012 | Stefanchik et al. |
| 2012/0130401 A1 | 5/2012 | Barrier et al. |
| 2012/0143173 A1 | 6/2012 | Steege et al. |

(Continued)

FOREIGN PATENT DOCUMENTS

| | | |
|---|---|---|
| CN | 101594816 | 12/2009 |
| CN | 102665589 | 9/2012 |

(Continued)

OTHER PUBLICATIONS

Communication Pursuant to Article 94(3) EPC dated Oct. 2, 2017 From the European Patent Office Re. Application No. 14840752.1. (6 Pages).

(Continued)

*Primary Examiner* — Jake Cook

(57) ABSTRACT

A control unit for a medical device is provided. The control unit includes a palm interface engageable by a palm of a hand, a restraint capable of elastically deforming to apply a restraining force to the dorsum of the hand and a finger interface engageable by one or more fingers of said hand.

20 Claims, 23 Drawing Sheets

(56) References Cited

U.S. PATENT DOCUMENTS

2012/0253326 A1    10/2012    Kleyman
2013/0150833 A1    6/2013    Peine et al.

FOREIGN PATENT DOCUMENTS

| | | |
|---|---|---|
| EP | 1584300 | 10/2005 |
| EP | 1836986 | 9/2007 |
| EP | 2005914 | 12/2008 |
| JP | 10-504984 | 5/1998 |
| JP | 2005-511334 | 4/2005 |
| JP | 2005-312919 | 11/2005 |
| JP | 2007-526805 | 9/2007 |
| JP | 2010-503457 | 2/2010 |
| JP | 2013-510671 | 3/2013 |
| WO | WO 2011/060139 | 5/2011 |
| WO | WO 2012/127404 | 9/2012 |
| WO | WO 2012/127462 | 9/2012 |
| WO | WO 2015/029041 | 3/2015 |

OTHER PUBLICATIONS

International Preliminary Report on Patentability dated Mar. 10, 2016 From the International Bureau of WIPO Re. Application No. PCT/IL2014/050781.

International Search Report and the Written Opinion dated Dec. 31, 2014 From the International Searching Authority Re. Application No. PCT/IL2014/050781.

Supplementary European Search Report and the European Search Opinion dated Jan. 20, 2017 From the European Patent Office Re. Application No. 14840752.1. (12 Pages).

Notification of Office Action and Search Report dated Jul. 18, 2017 From the State Intellectual Property Office of the People's Republic of China Re. Application No. 201480053589.X and Its Summary in English. (9 Pages).

Translation of Notification of Office Action dated Jul. 18, 2017 From the State Intellectual Property Office of the People's Republic of China Re. Application No. 201480053589.X. (5 Pages).

Examination Report dated May 22, 2018 From the Australian Government, IP Australia Re. Application No. 2014313763. (6 Pages).

Notification of Office Action dated Feb. 24, 2018 From the State Intellectual Property Office of the People's Republic of China Re. Application No. 201480053589.X. (7 Pages).

Translation Dated Mar. 12, 2018 of Notification of Office Action dated Feb. 24, 2018 From the State Intellectual Property Office of the People's Republic of China Re. Application No. 201480053589. X. (7 Pages).

Notice of Reasons for Rejection dated Apr. 17, 2018 From the Japan Patent Office Re. Application No. 2016-537601 and Its Translation Into English. (7 Pages).

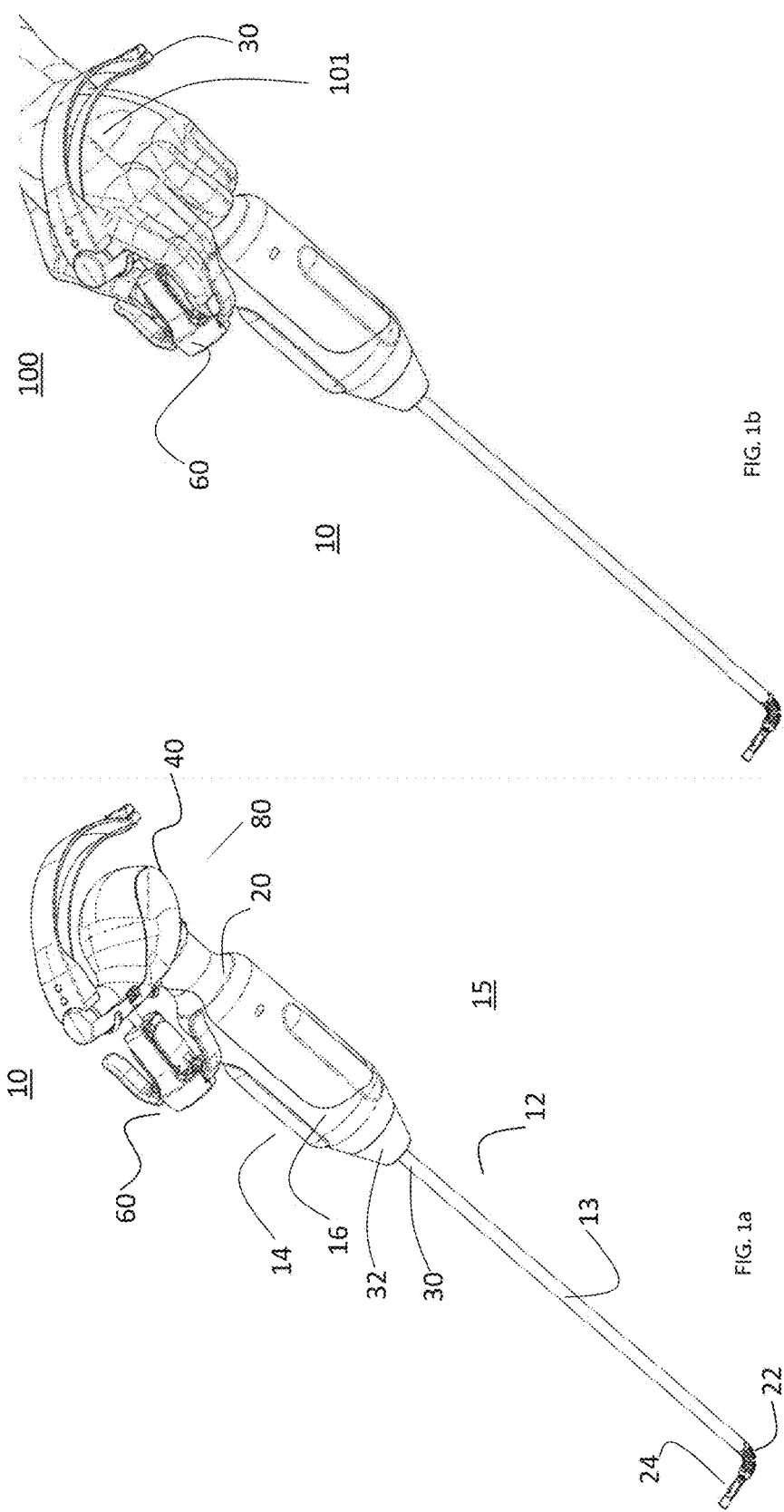

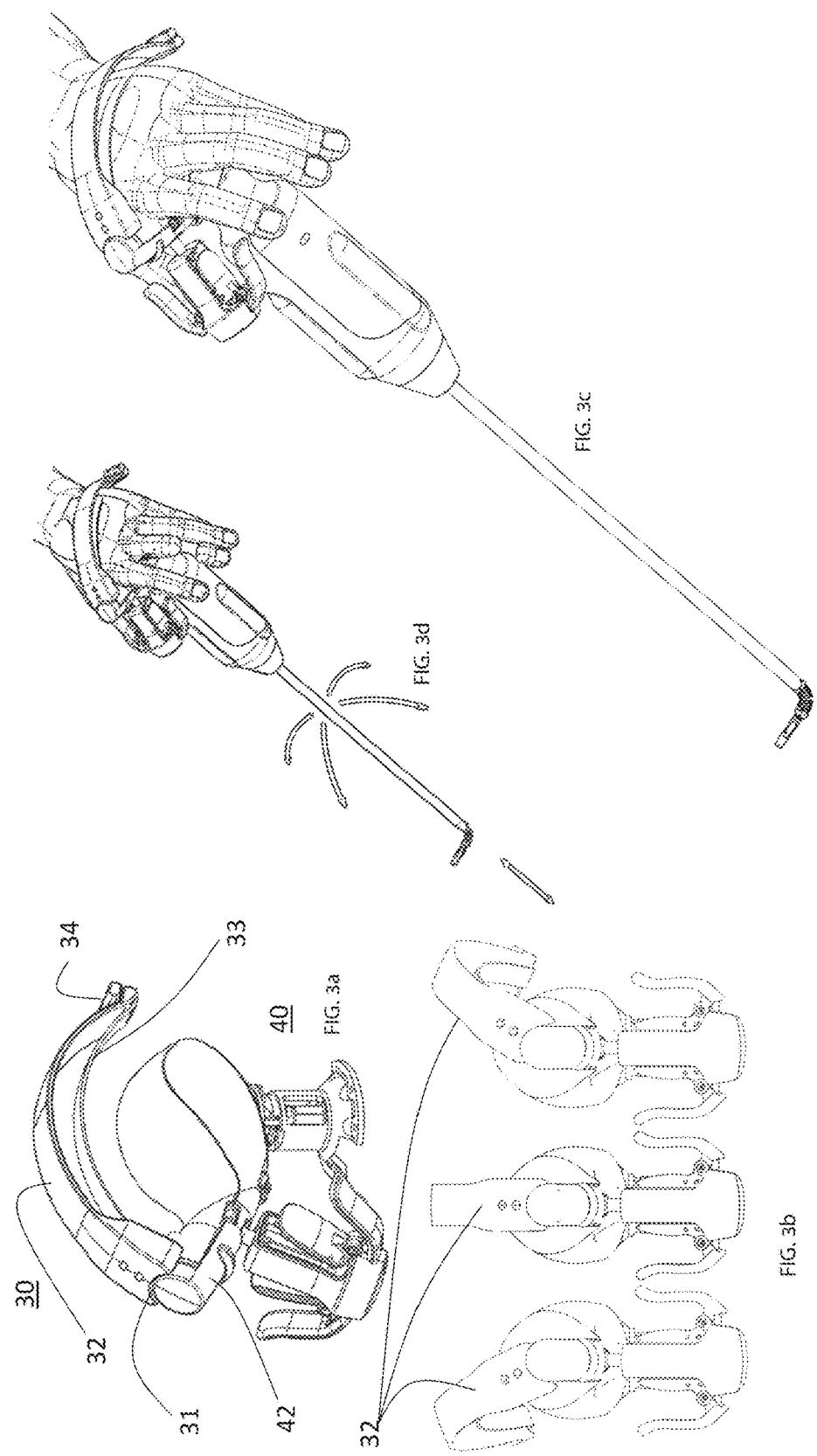

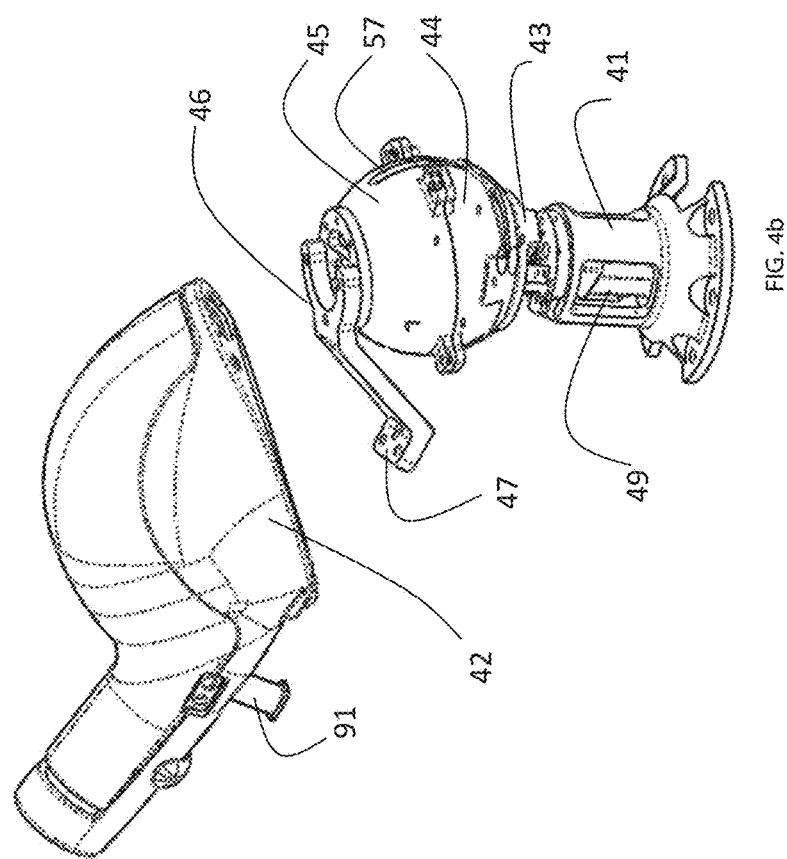
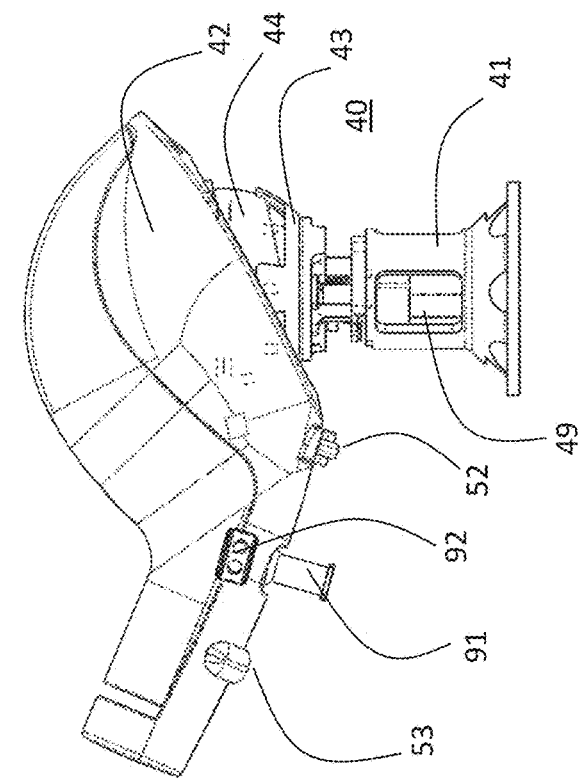
FIG. 4b
FIG. 4a

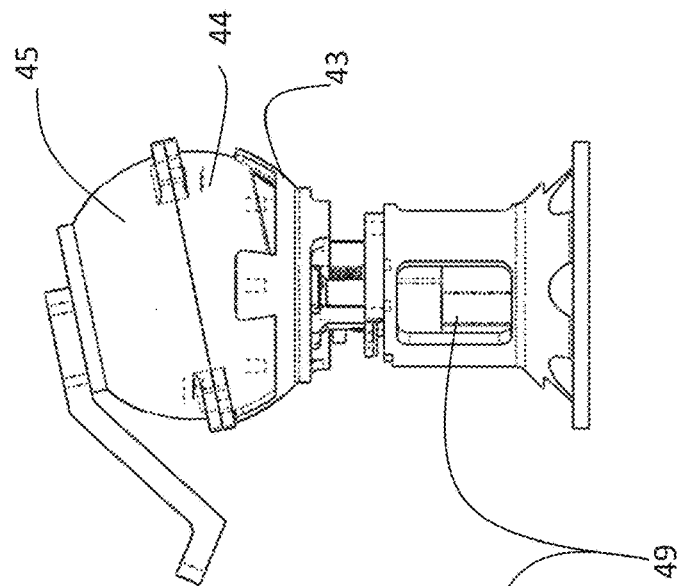
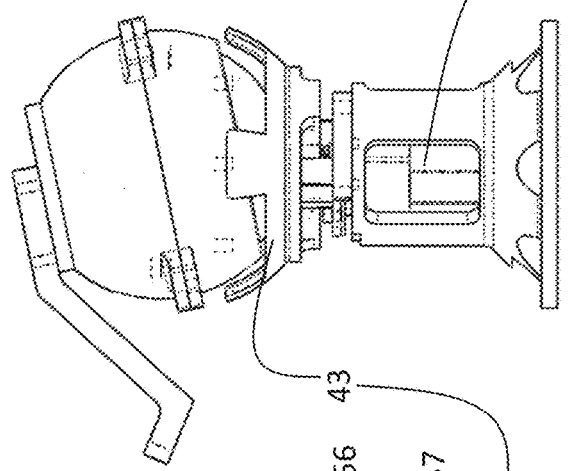
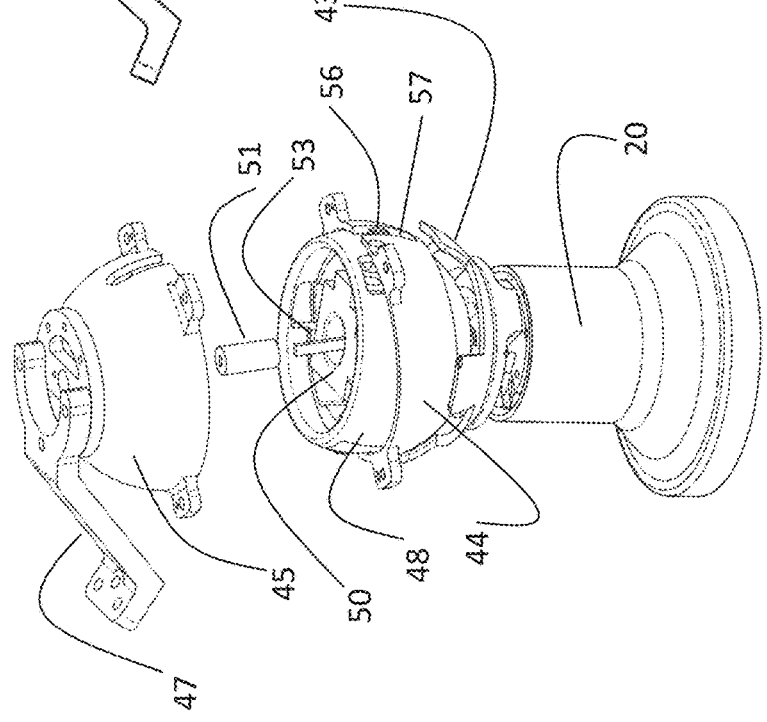
FIG. 4e
FIG. 4d
FIG. 4c

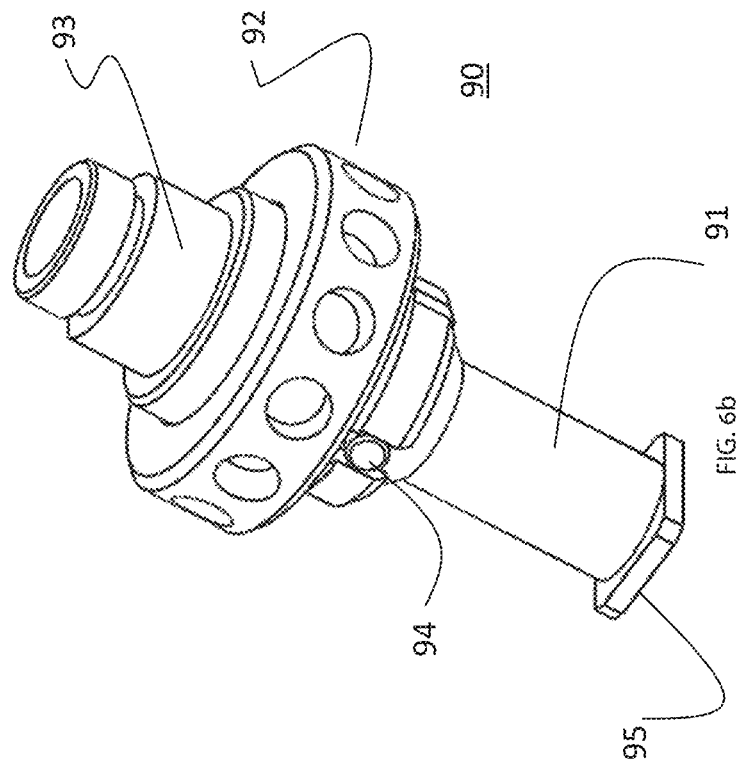
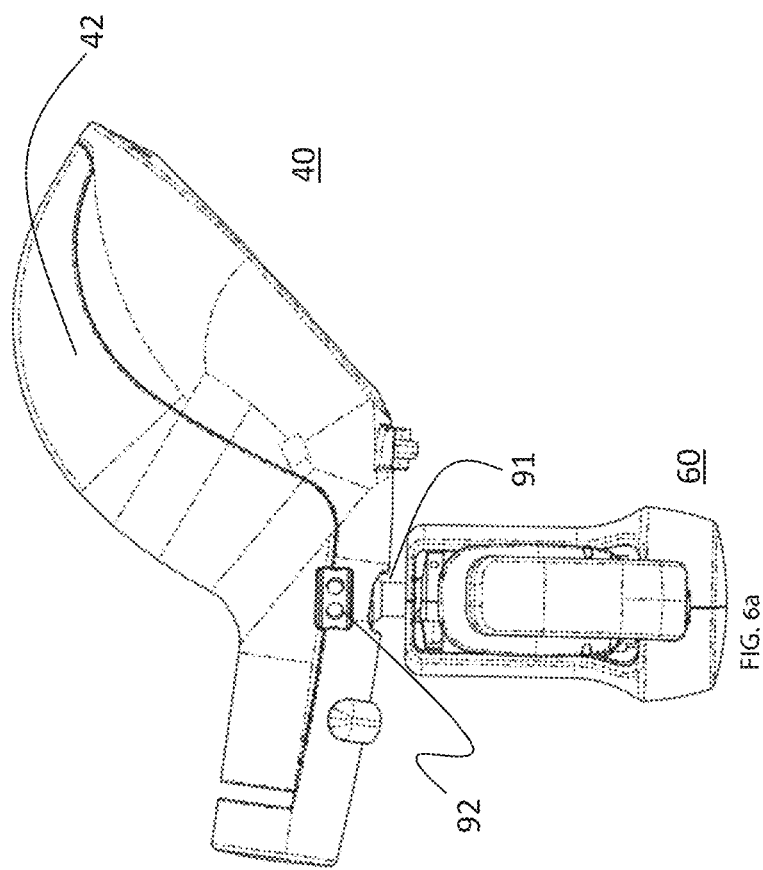

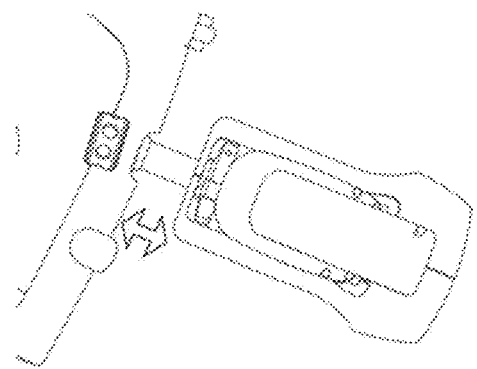
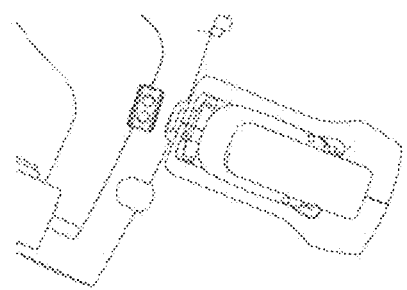
FIG. 7b
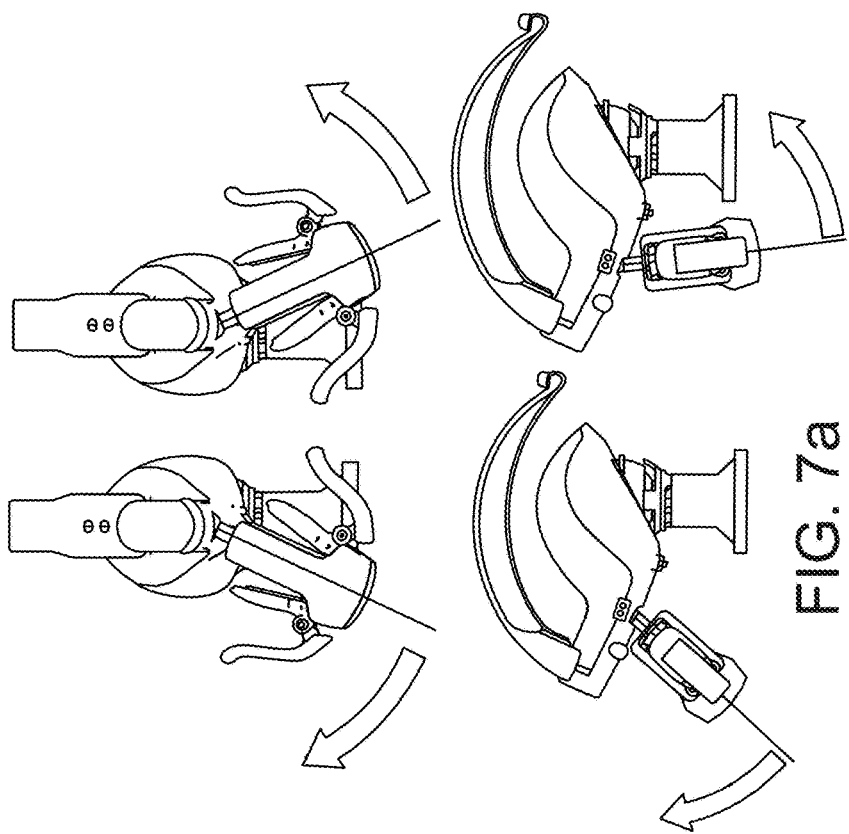
FIG. 7a

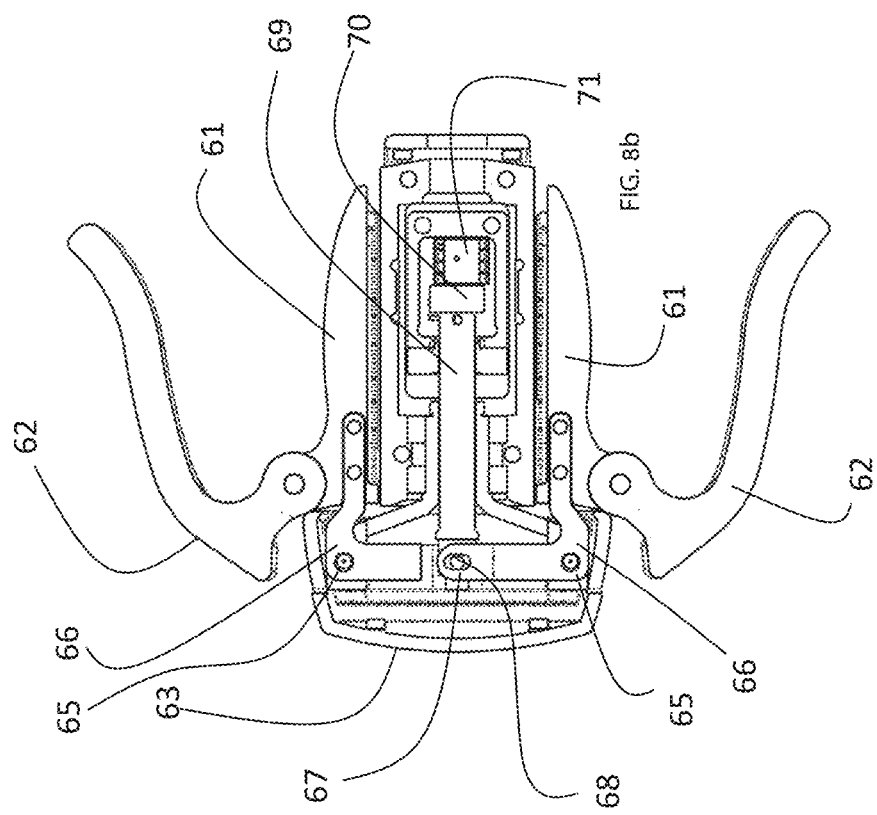
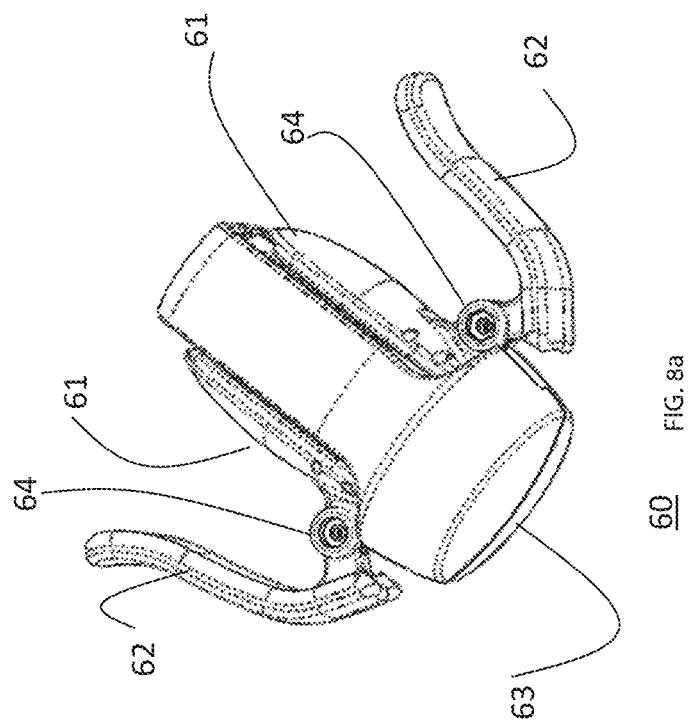

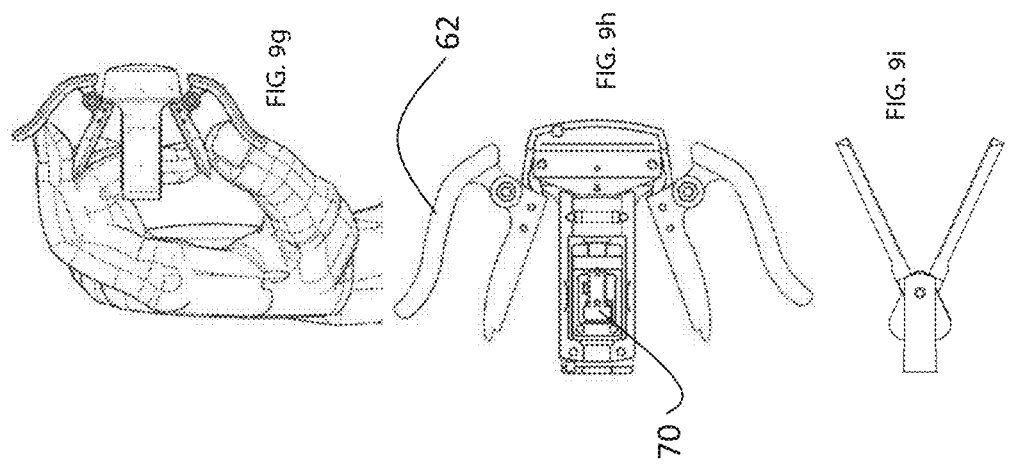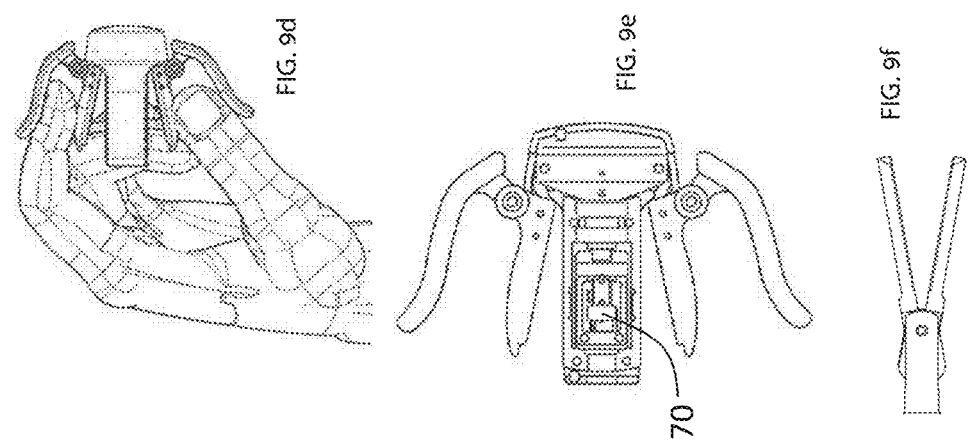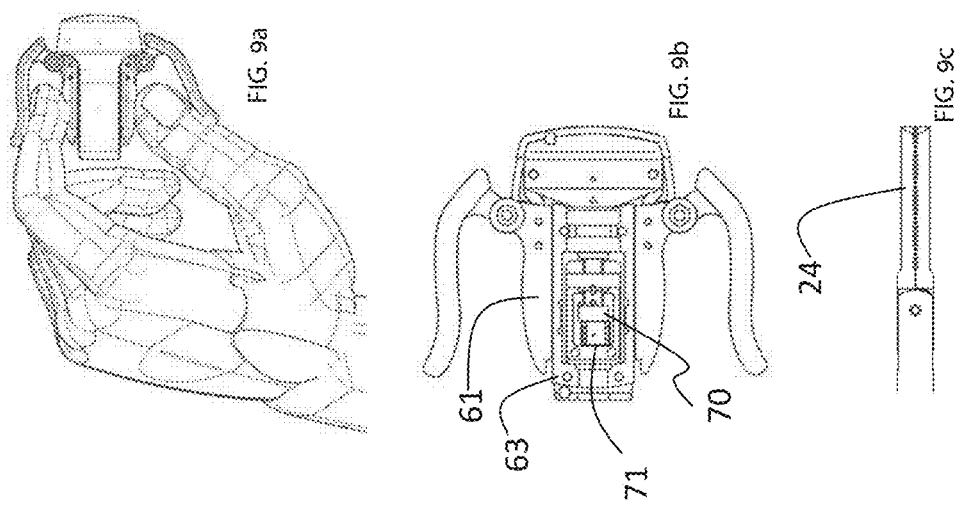

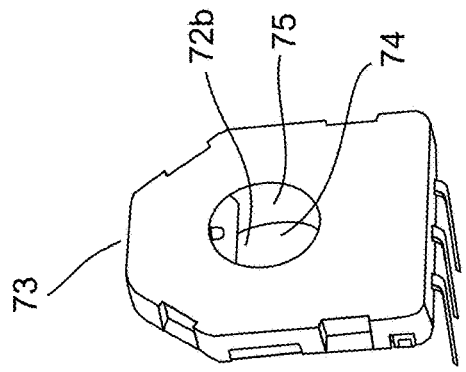
FIG. 10c
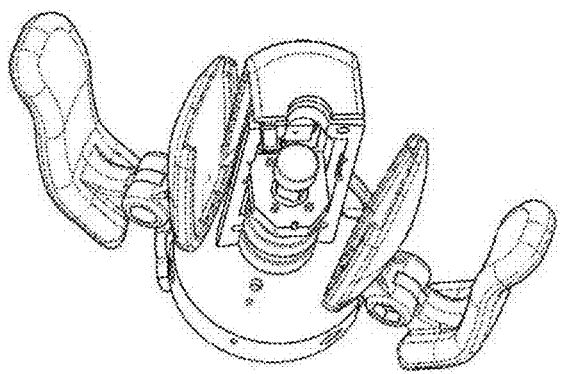
FIG. 10b
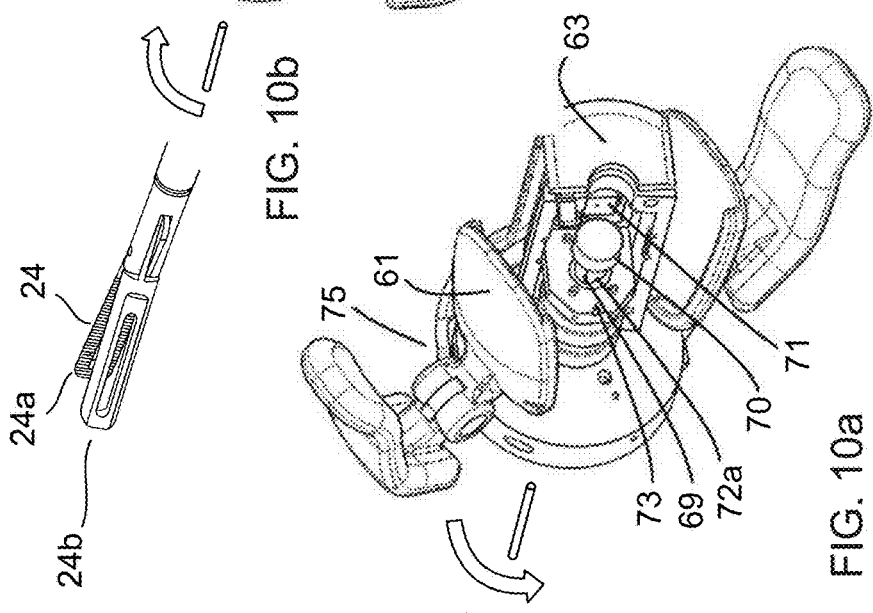
FIG. 10a
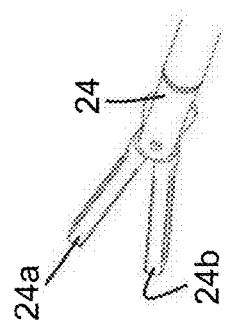

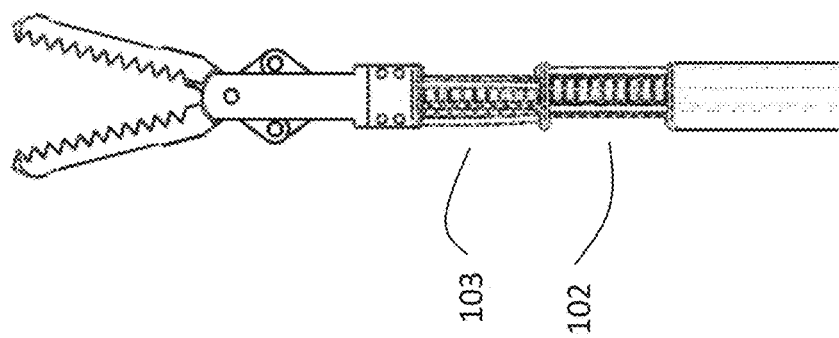
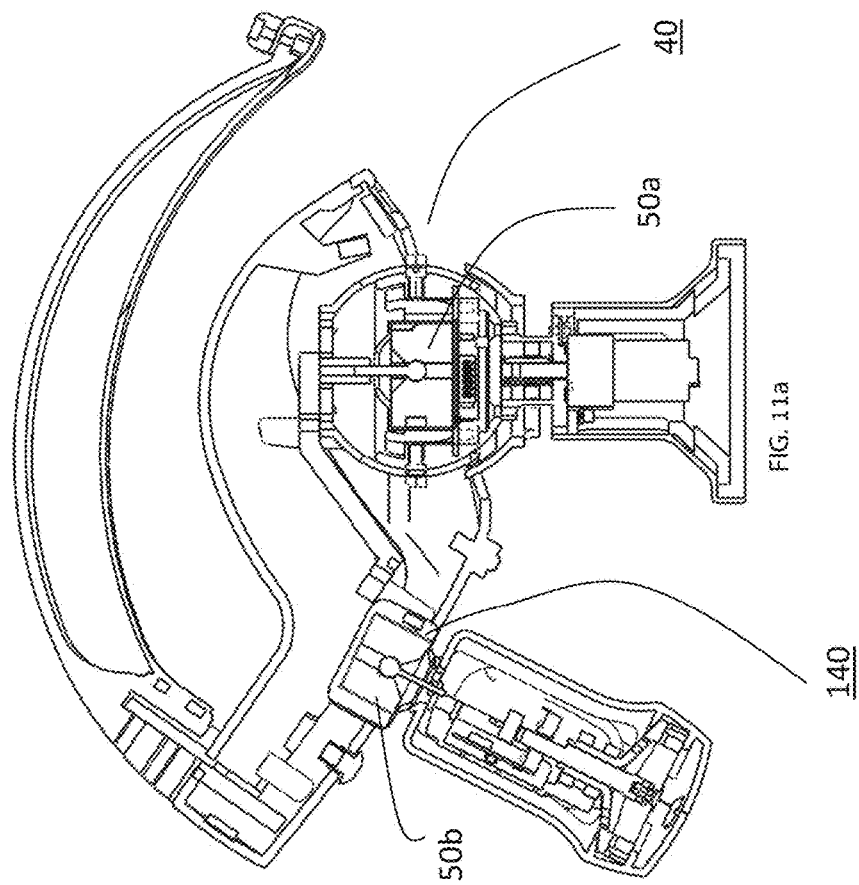

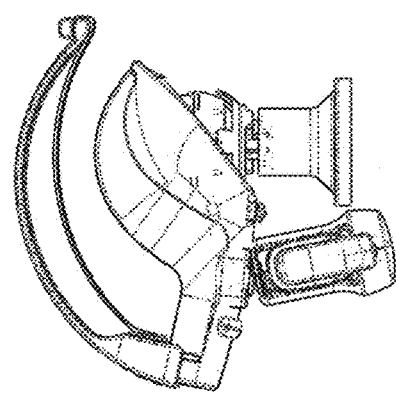
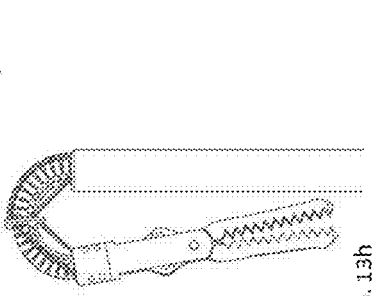
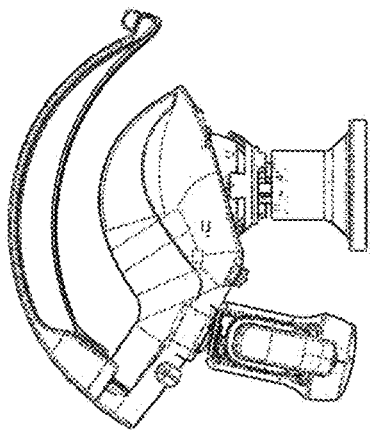
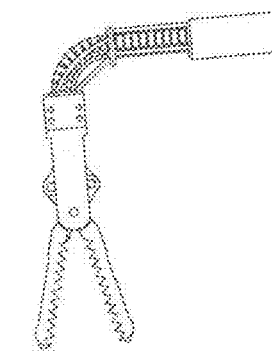
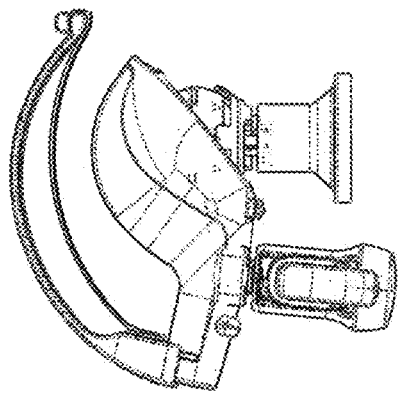
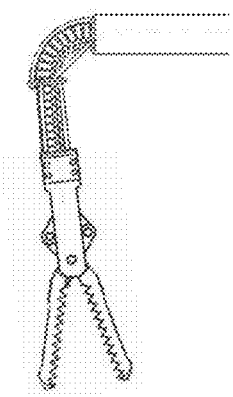
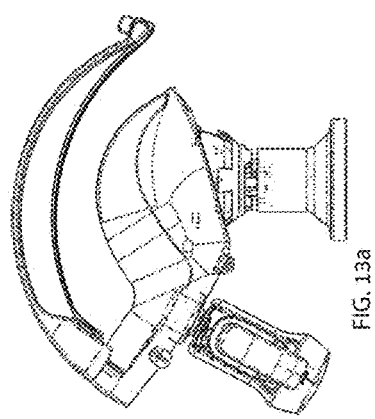
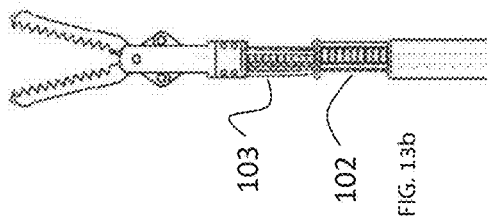

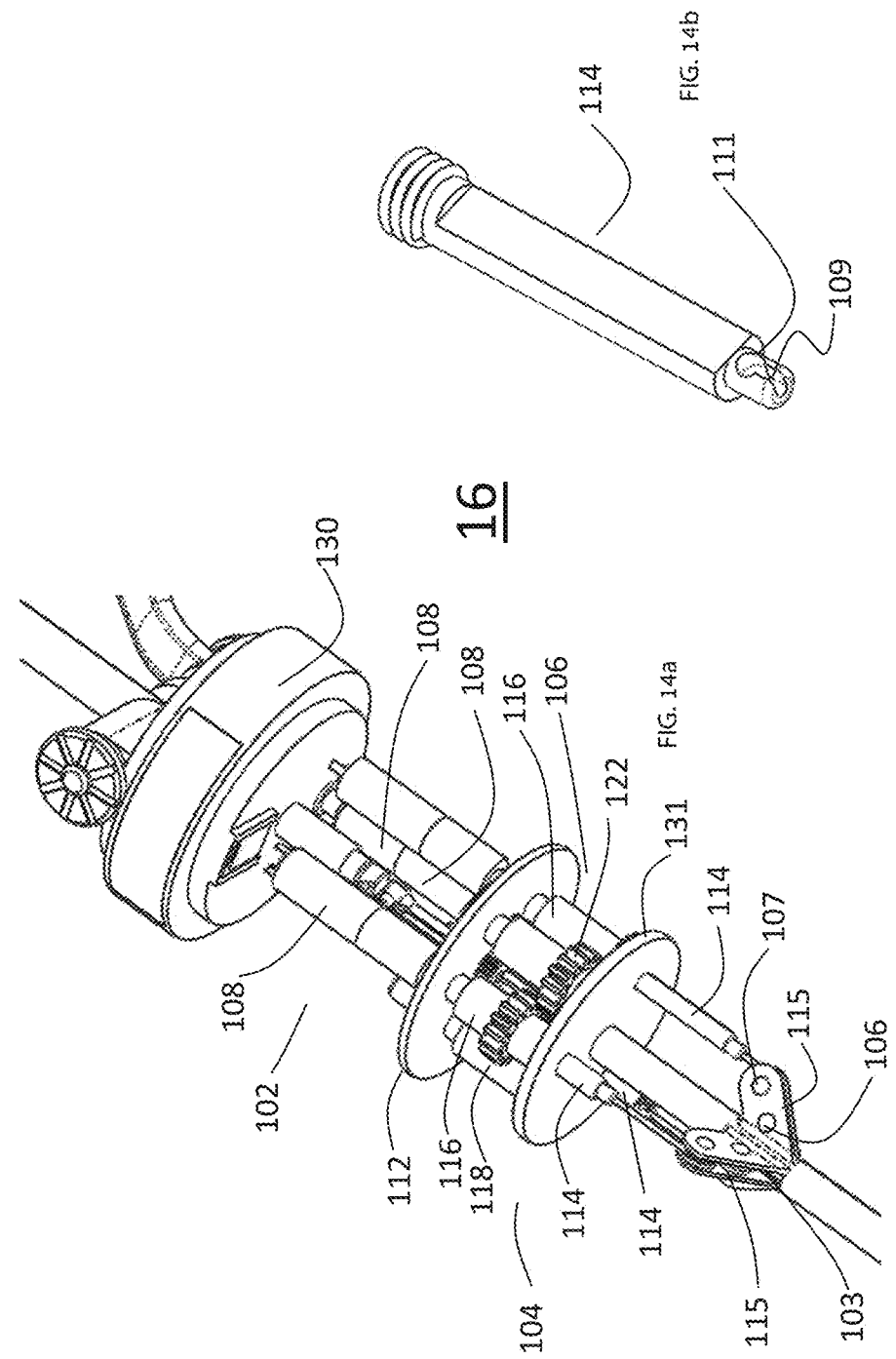

CONTROL UNIT FOR A MEDICAL DEVICE

RELATED APPLICATIONS

This application is a National Phase of PCT Patent Application No. PCT/IL2014/050781 having International filing date of Sep. 1, 2014, which claims the benefit of priority under 35 USC § 119(e) of U.S. Provisional Patent Application Nos. 61/972,528 filed on Mar. 31, 2014 and 61/872,727 filed on Sep. 1, 2013. The contents of the above applications are all incorporated by reference as if fully set forth herein in their entirety.

FIELD AND BACKGROUND OF THE INVENTION

The present invention relates to a control unit for a medical device and, more particularly, to a control unit and integrated user interface which enable translation of natural hand movements to an attached medical tool such as a laparoscopic tool to thereby enable precise and fine control over the position and function of the medical device.

Medical devices such as endoscopes and catheters are widely used in minimally invasive surgery for viewing or treating organs, cavities, passageways, and tissues. Generally, such devices include an elongated device body which is designed for delivering and positioning a distally-mounted instrument (e.g. scalpel, grasper or camera/camera lens) within a body cavity, vessel or tissue.

Since such devices are delivered through a delivery port which is positioned through a small incision made in the tissue wall (e.g. abdominal wall), and are utilized in an anatomically constrained space, it is desirable that the medical device or at least a portion thereof be steerable, or maneuverable inside the body using controls positioned outside the body (at the proximal end of the medical device). Such steering enables an operator to guide the device within the body and accurately position the distally-mounted instrument at an anatomical landmark.

Various interfaces for endoscopic instruments have been described in the prior art, see, for example, U.S. Patent Application Nos. 2008/0255420 and 2012/0041450 and U.S. Pat. No. 7,572,253.

However, there remains a need for a medical device control unit having an interface that allows the surgeon to intuitively maneuver a surgical tool inside the body while allowing precise control through a wide range of device and effector-end movements.

SUMMARY OF THE INVENTION

According to one aspect of the present invention there is provided a control unit for a medical device, the control unit comprising a user interface including (a) a first interface being mounted on a pivotal support attached to a housing of the control unit, the first interface being engageable by a palm of a hand; (b) a restraint being pivotally attached to the first interface and having an element capable of elastically deforming to apply a restraining force to a back of the hand when the palm is engaged with the first interface; and (c) a second interface being pivotally attached to the first interface and being engageable by one or more fingers of the hand.

According to further features in preferred embodiments of the invention described below, the pivotal support is gimbaled.

According to still further features in the described preferred embodiments the control unit further comprises a housing including a drive unit.

According to still further features in the described preferred embodiments the second interface includes levers are sequentially or simultaneously operable via thumb and index finger of the hand.

According to still further features in the described preferred embodiments the first interface can be tilted with respect to the pivotal support.

According to still further features in the described preferred embodiments tilting of the first interface deflects a steerable portion of the medical device.

According to still further features in the described preferred embodiments the levers operate an effector end of the medical device.

According to still further features in the described preferred embodiments the second interface can be tilted with respect to the first interface.

According to still further features in the described preferred embodiments tilting of the second interface deflects an effector end of the medical device.

According to still further features in the described preferred embodiments the drive unit includes at least one motor and control wires for operating the medical device.

According to another aspect of the present invention there is provided control unit for a minimally invasive surgical tool, the control unit comprising a user interface including: (a) a first interface control being engageable by a back of a hand of a user and being for controlling an angle and height of the minimally invasive surgical tool with respect to a tissue access site; (b) a second interface control being engageable by a palm of the hand of the user and being for controlling a deflection of a steerable portion of the minimally invasive surgical tool; and (c) a third interface control being engageable by one or more fingers of the user and being for controlling a tissue manipulating end of the minimally invasive surgical tool.

According to still further features in the described preferred embodiments the control unit further comprises a housing including a drive unit.

According to still further features in the described preferred embodiments the second interface control is gimbaled.

According to still further features in the described preferred embodiments the first interface control includes an arm hingedly connected to a dorsum pad.

According to still further features in the described preferred embodiments the control unit further comprises a knob for rotating the housing with respect to the first, second and third interface controls.

According to still further features in the described preferred embodiments the third interface control includes a pair of finger holds operable via a thumb and index finger.

According to still further features in the described preferred embodiments the third interface control includes a ball rotatable around at least two perpendicular axis.

According to still further features in the described preferred embodiments a user can simultaneously operate the first, second and third interface controls via a single hand.

According to still further features in the described preferred embodiments the drive unit includes at least one motor for operating the minimally invasive laparoscopic tool.

According to still further features in the described preferred embodiments the control unit further comprises a strap or clamp for securing the hand of the user to the first interface control.

The present invention successfully addresses the shortcomings of the presently known configurations by providing a control unit for a surgical tool such a laparoscope. The control unit includes a user interface that enables a user to simultaneously control the movement and actuation of an attached surgical tool such as a laparoscope using a single hand.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1a-c illustrate one embodiment of the control unit of the present invention attached to a laparoscope. FIG. 1a is a general view of motorized laparoscopic tool and the surgeon interface, FIG. 1b illustrates positioning of the surgeon's hand within the surgeon interface. FIG. 1c shows the laparoscopic tool without the motor pack cover.

FIGS. 3a-d illustrate the dorsum interface portion of the present invention.

FIGS. 4a-g illustrate the palm interface portion and the palm interface mechanical components including an exemplary joystick component (FIG. 4g) of the present invention.

FIGS. 6a-b illustrate one embodiment of the finger interface portion of the present invention.

FIGS. 7a-b illustrate the surgeon options for ergonomic adjustments of the finger interface portion of the present invention.

FIGS. 8a-d illustrate the finger interface portion of the present invention and related components.

FIGS. 9a-i illustrate jaws open-close modes enabled by the finger interface portion of the present invention.

FIGS. 10a-b illustrate jaw rotational modes enabled by the finger interface portion of the present invention.

FIG. 10c is a sensor utilizable by the finger interface of the present control unit.

FIGS. 11a-b illustrate an embodiment of the present invention which enables simultaneous control over two steerable portion of an attached laparoscope. FIG. 11a is a cut-away view of the interface, showing a sensor for enabling control of a second steerable portion. FIG. 11b illustrates articulation with 2 independent steerable portions.

FIGS. 13a-h illustrate interface controls over two independent steerable portions.

FIGS. 14a-b, FIG. 15 and FIG. 16 illustrate a motorized drive unit embodiment of the control unit of the present invention.

DESCRIPTION OF THE PREFERRED EMBODIMENTS

Figure 1C:
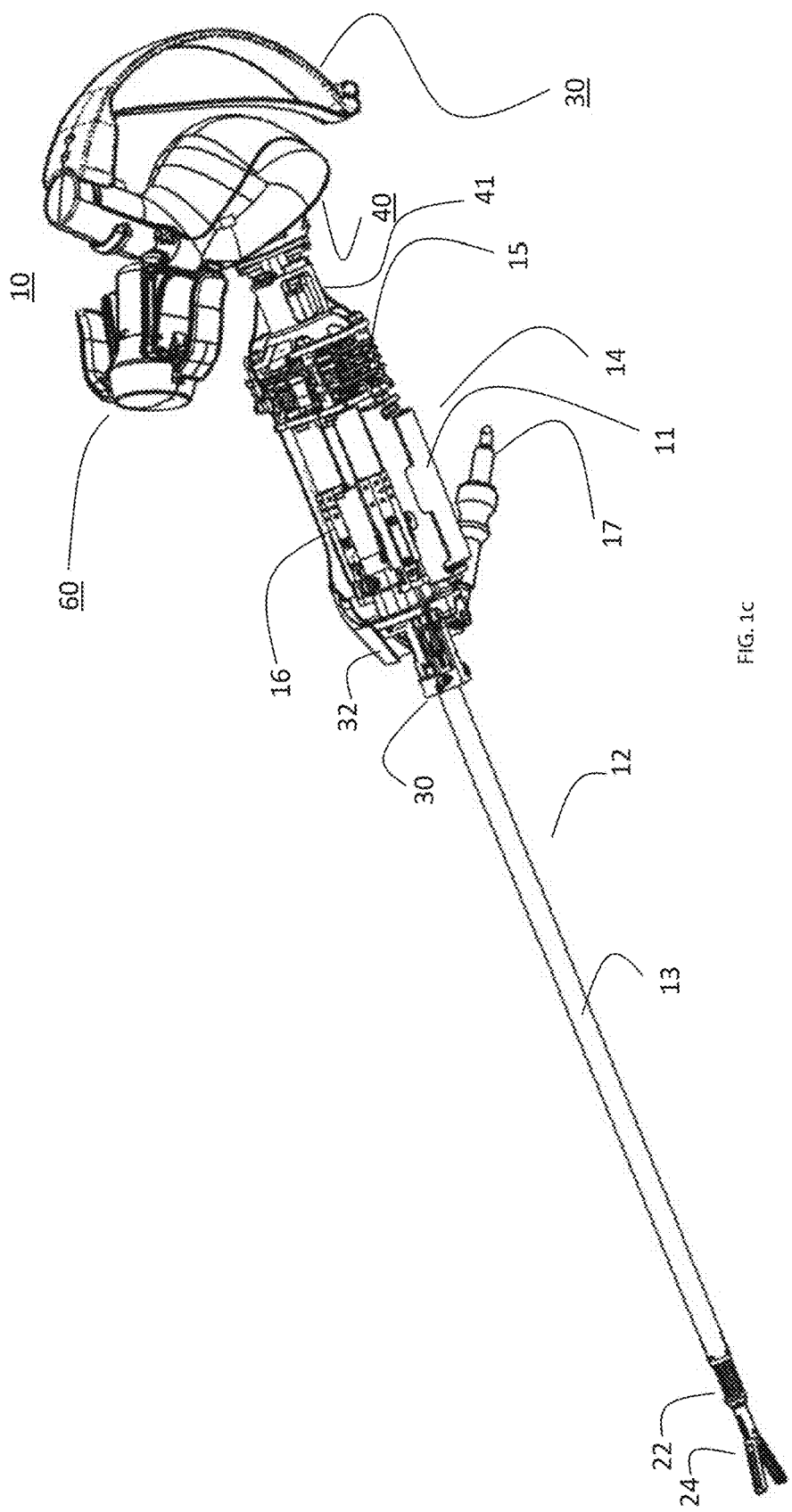

The present invention is of a control unit and interface which can be used to control the movement, position and function of an attached medical device. Specifically, the present invention can be used to control a surgical tool such a laparoscope using natural hand movements.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

In laparoscopic surgery, a surgeon has to position the distal end portion (including the tissue manipulating end, e.g., grasper) of the laparoscope within a body cavity (e.g. abdominal cavity) and adjacent to treated tissue. In order to correctly position the laparoscope, the surgeon has to spatially orient the entire laparoscope while controlling deflection of the steerable portion and actuating the tissue manipulating end.

A surgeon typically uses an interface (handle) of a surgical tool for positioning, maneuvering, holding and operating the device and effector end at the tissue site of interest. While presently used device interfaces can provide such functionality, they can be limited by a tradeoff between maneuverability and operability of the entire device and its effector end (instrument mounted on a distal end of a laparoscope shaft) thus requiring considerable time and effort on the part of the surgeon to complete a minimally invasive treatment procedure.

Experiments performed using various prototypes of the laparoscopic tool interface described herein have led to the development of a control unit and interface that can provide a surgeon with more natural and complete control over the operation of a medical device such as a laparoscope.

Thus, according to one aspect of the present invention there is provided a control unit for a medical device.

The control unit includes a drive unit and attached user interface. As is further described hereinunder, the interface is operated by a single hand of a user and actuates motors and control wires within the control unit to thereby control positioning, movement and operation of a medical device attached to the control unit.

The control unit includes a user interface which has separate control for device positioning, movement and effector end positioning and operation. The user interface includes a first interface which is mounted on a pivotal support attached to a housing of the control unit. The first interface is engageable by a palm of a hand and enables the user to control deflection of a steerable portion of the medical device as well as rotation and tilting (with respect to tissue access site) of the entire device.

To maintain the palm of a user against the first interface through tilting, rotation and angulation, the control unit further includes a restraint which is pivotally attached to the first interface and includes an element that is capable of elastically deforming to apply a restraining force to a back of the hand (dorsum) when the palm is engaged with the first interface. When this restraint engages the back of the hand, the element elastically deforms and applies a downward force to the back of the hand thus maintaining the hand against the first interface and enabling precise control of this interface, as well as, enabling the user to pull up on the medical device.

The control unit also includes a second interface which is pivotally attached to the first interface and is engageable by one or more fingers of the hand.

The user interface of the present invention is suitable for use with any medical device used for viewing or manipulating tissue at a site of treatment in or on the body of a mammal (e.g. human subject).

The medical device of the present invention is preferably used in minimally invasive surgery wherein a steerable distal portion thereof positioned within a body of a subject is controlled from a proximal end positioned outside the body (extra corporeally) via, for example, control wires. The medical device can be used for viewing or for manipulating tissues within any body cavity. Examples of medical devices that can benefit from the present invention include an endoscope (e.g. laparoscope or thorascope), a catheter, a surgical holder and the like.

The user interface of the present invention is particularly suitable for use with a laparoscopic device having a steerable distal portion and a distally-mounted instrument such as a grasper or cutter.

Laparoscopes are widely used in minimally invasive surgery for viewing or treating organs, cavities, passageways, and tissues. Generally, such devices include an elongated device body which is designed for delivering and positioning a distally-mounted instrument (e.g. scalpel, grasper or camera/camera lens) within a body cavity, vessel or tissue.

Since such devices are delivered though a delivery port which is positioned through a small incision made in the tissue wall (e.g. abdominal wall), and are utilized in an anatomically constrained space (within, for example, the abdominal cavity), it is desirable that the medical device or at least a portion thereof be steerable, or maneuverable inside the body using controls positioned outside the body (at the proximal end of the medical device). Such steering enables an operator to guide the device within the body and accurately position the distally-mounted instrument at an anatomical landmark.

Numerous examples of steerable devices are known in the art, see for example, U.S. Pat. Nos. 2,498,692; 4,753,223; 6,126,649; 5,873,842; 7,481,793; 6,817,974; 7,682,307 and U.S. Patent Application Publication No. 20090259141.

Deflection of the steerable portion is typically effected via one or more control wires which run along the shaft of the device to the distal end of the steerable portion.

The proximal end of each control wire is connected to the control unit; pulling of the wire applies forces that deflect the steerable portion with relation to the pulled wire.

The device effector end (distally-mounted instrument) is controlled via one or more additional wires which are similarly connected to the control unit and actuated by the user interface. Thus, the user interface and control unit of a steerable device such as a steerable laparoscope provides three separate functions, positioning of the device shaft with respect to the tissue access site (up/down, angle), deflection of the steerable portion, and actuation of the distally mounted instrument.

The user interface of the present invention provides these three functions via movement of three separate limb joint and muscle groups.

(i) The shaft of the device is moved up and down and side to side with respect to the tissue access site by arm movement (primarily about the elbow and/or shoulder joints).

(ii) The steerable portion of the device shaft is deflected via hand movement (primarily about the wrist joint). This is achieved by tilting the first interface.

(iii) The distally mounted instrument is actuated via finger movement (primarily about the inter-phalangeal joints and the metacarpal-phalangeal joints). Finger movement can also be used to deflect the device shaft around a second deflection region.

The present interface provides several advantages when used to position and operate a surgical tool such as a steerable laparoscope:

(i) greater and more natural maneuverability—a laparoscope can be operated using less effort and without requiring extreme maneuvering of body and limbs;

(ii) simultaneous control over the three functions—the laparoscope can be positioned while being steered and actuated;

(iii) single handed operation—all movements are controlled via a single hand using three interface regions, the dorsum, the palm and the fingers;

(iv) single handed operation of multiple steerable portions—all movements are controlled via a single hand operating simultaneously three interface regions, the dorsum, the palm and the fingers;

(v) compact interface fits in the palm of a hand, instinctive operation shortens learning curve; and (vi) can be used to control any attached/integrated surgical instrument.

The control unit and interface of the present invention are described in more detail below with reference to FIG. 1a-13h.

FIGS. 1a-b illustrate control unit 10 attached to surgical tool 12. For illustrative purposes control unit 10 is shown attached to a laparoscope 12 in FIG. 1a with a hand 100 of a user engaged with user interface 80 of control unit 10 (FIG. 1b). It will be understood however, that control unit 10 (or only interface 80 thereof) can be attached to, or integrated with, any surgical instrument that can benefit from the present invention.

Control unit 10 includes a housing 14 which contains a drive unit 16 circuitry 15 shown in FIG. 1c and an interface 80 which is mounted on a proximal end 20 of housing 14. Housing 14 and interface 80 can be fabricated from a polymer and/or alloy using machining, 3D printing and/or casting/molding fabrication approaches. Housing 14 can be 40-60 mm in diameter and about 60-120 mm in height.

Laparoscope 12 includes a shaft 13 having a steerable portion 22 and a distally mounted instrument (grasper 24 shown). Laparoscope can be fabricated using materials and approaches well known in the art.

Shaft 13 includes a plurality of wire guides (not shown) disposed along its length for routing one or more control wires (not shown) from drive unit 14 to an end of the steerable portion and one or more actuation wires from drive unit 14 to grasper 24. In the case of a device which includes two or more separately steerable portions (e.g. enabling zigzag-shaped deflection), each control wire is routed to an end of a respective steerable portion.

Shaft 13 can be 20-40 cm in length and 3-12 mm in diameter and can be hollow or solid. A hollow shaft 13 enables internal routing of wires, in a solid configuration of shaft 13, wires can be routed on the external surface of shaft 13 through dedicated guides.

The steerable portion of shaft 13 can be fabricated from a tube having cutouts (e.g. such as those shown in U.S. Pat. No. 4,911,148) or from links (e.g. U.S. Pat. No. 7,682,307, U.S. Pat. No. 6,817,974) with control wires running through guides formed in the tube or links. Alternatively, the steerable portion can be fabricated as described in U.S. Provisional Patent Application No. 61/765,745 to the present inventor, the teachings of which are fully incorporated herein.

Proximal end 30 of shaft 13 is attached to a distal end 32 of housing 14, and control and actuation wires/rods of shaft 13 run through housing 32 and attach to drive unit 16. Drive unit 16 can include levers and gears for translating movements of user interface 80 to pulling of control and/or actuation wires. Such transfer can be mechanical (manual) or motorized. A motorized embodiment of drive unit 16 is shown in FIG. 1c and FIGS. 14a-b and 15-16.

FIG. 1b illustrates engagement between hand 100 of a user and interface 80. The surgeon's hand 100 is placed in such a manner where the back of the user's hand (herein dorsum 101) is positioned under restraint 33 (of dorsum interface 30) while three of the user's fingers are free to grasp first interface 40 (also referred to herein as palm interface 40), the thumb and index fingers engage a second interface 60 (also referred to herein as finger interface 60).

FIG. 1c illustrates control unit 10 with housing cover removed showing drive unit and associated components. Drive unit 16 includes a motor pack, battery 11, the electrical circuits of controller 15 and base 41 of palm interface 40. Diathermia plug 17 is shown connected to the device body.

Figure 2B:
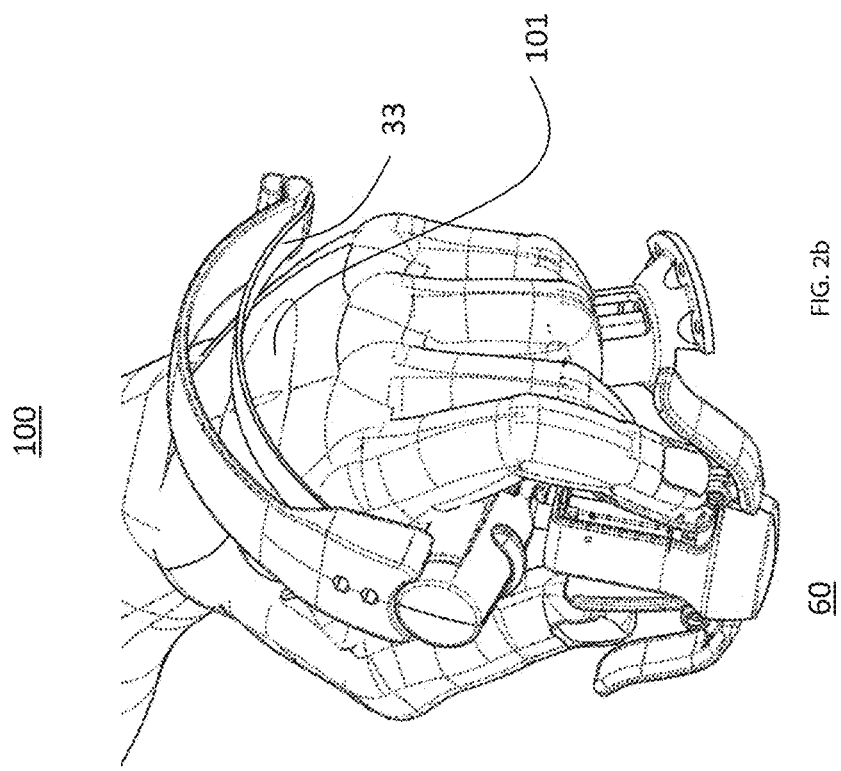
FIGS. 2a-b illustrate the interface portion of the interface (FIG. 2a) and a user's hand mounted thereon.
Figure 2A:
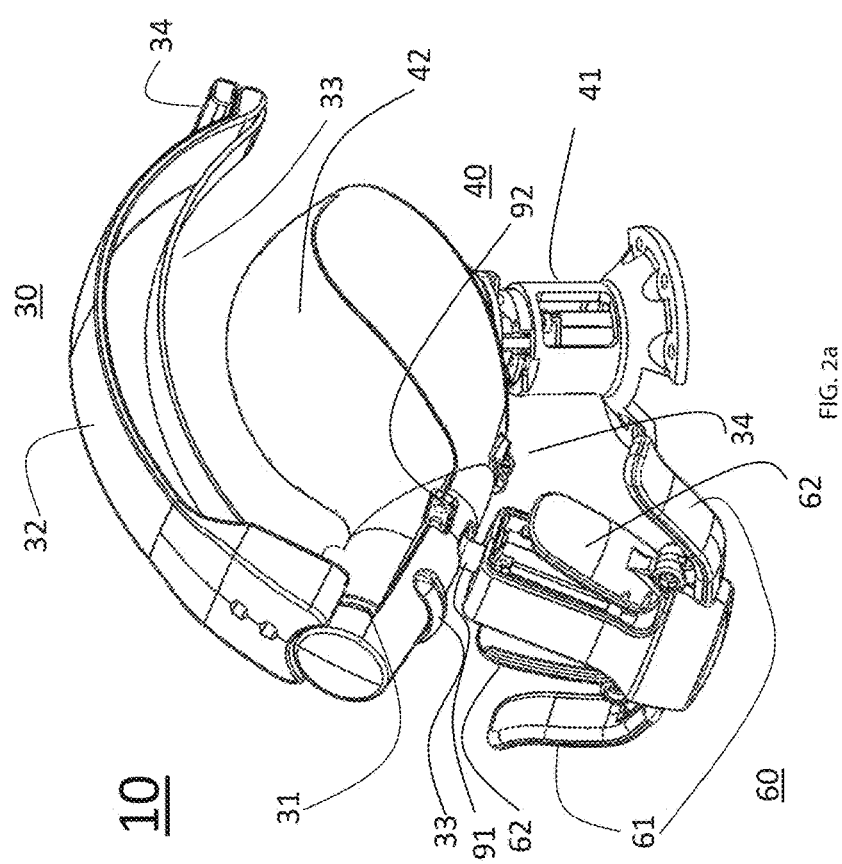

FIG. 2a illustrates the three control interfaces of user interface 80 in greater detail; dorsum interface 30, palm interface 40 and finger interface 60.

Dorsum interface 30 includes two arc-shaped elements 32 and 33 that are interconnected at their ends. Element 33 engages dorsum 101 and is elastically deformable to conform to dorsum 101 while applying a downward force thereto. Element 32 is preferably rigid but can have some elasticity. Dorsum interface 30 is connected to palm interface 40 at 31. Dorsum interface 30 may be immovably attached to base 41 or it may freely rotate with respect to base 41 thereby adjusting to the manner in which a user's hand fits against (on top of) palm interface 42.

Palm interface 40 is pivotally attached to a base 41 which includes sensors for measuring the spatial orientation of the user's hand, by measuring the orientation of palm surface 42 with respect to base 41.

Finger interface 60 is connected to palm interface 40 via shaft 91. Shaft 91 form a part of a ball joint 90 (not visible) that allows shaft 91 to spatially rotate with respect to palm interface 40. The movement of shaft 91 allows the user to adjust the orientation of finger interface 60 in order to achieve optimal ergonomics.

Knob 92 allows the user to adjust the frictional force on ball joint 90, allowing to fixate finger interface 60 with respect to palm interface 40 or to enable the user to change the orientation of finger interface 60 at any time.

Finger interface 60 is used to control an effector end (e.g. surgical tool such as grasper) of the device. Finger interface 60 can simultaneously determine the distance between the user's fingers and their orientation via sensors attached to the levers of this interface.

Figure 5E:
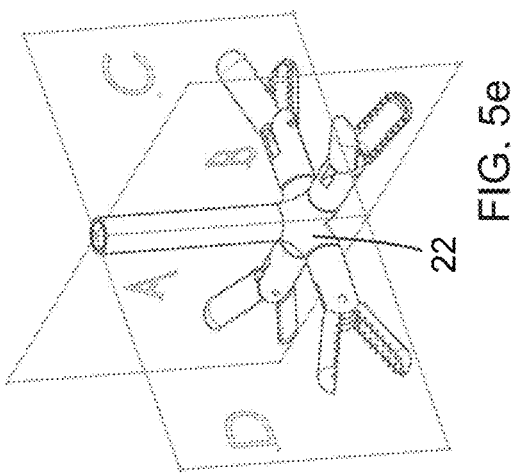
FIGS. 5a-e illustrate the movements of the palm interface and the corresponded movements of the articulation

FIG. 2b typical engagement between interface 80 and hand 100 of the user. The palm of the user rests against palm surface 42 of palm interface 40, dorsum 101 is positioned underneath dorsum interface 30 (and is forced downward by the elastic deformation of element 33), three of the user's fingers grasp the circumference of palm surface 42 and the other two fingers (thumb and index finger) engage (pinch) levers 62 of finger interface 60. While holding interface 80, the user can tilt palm surface 42, and open/close or rotate levers 62 of finger interface 60. While performing these movements, sensors locate at interface 40 and 60 measure the movement. The sensors measurements are sampled by controller 15. Controller 15 compares the orientation of palm surface 42 to the orientation of articulation 22 (FIG. 5e). If there is a difference the controller sends commands to the motors in order to change the orientation of articulation 22 to match that of the user's hand.

Finger interface 60 measures a distance between the thumb and index fingers engaging the levers, by measuring for example the angles of finger levers 62 of this interface. Controller 15 calculates the difference between the distance of the fingers and the distance between, for example, the jaws of a grasper effector end, and sends commands to the motor that operates the jaws open-close mechanism in order to match jaw opening to finger distance.

Rotational (twist) measurement is enabled via a rotation sensor (not shown) that measures the angle between finger interface 60 and shaft 91. Controller 15 calculates the difference between the angle of the fingers and the angle between the jaws and the shaft. If there is a difference between the measurements, controller 15 sends commands to the motor that operates the jaws rotation mechanism in order to match jaw rotation to finger angulation.

Some of the measurements sampled by controller 15 may be scaled in order to maintain optimal ergonomics. For example, the movement of a user's hand can be scaled up in order to provide large changes in shaft deflection via relatively small palm movements, or alternatively, movement of the user's hand can be scaled dawn to increase accuracy of movement.

As is described hereinabove, each of these interface elements serves a different control function and all three can be operated simultaneously to enable precise and intuitive control over laparoscopic tool 12, steerable portion 22 and effector end 24 (e.g. grasper).

In addition to the above, user interface 80 can also include buttons (on interface 40 or 60, or on housing of control unit 10) for operating a light source, diathermia device, camera and the like positioned within control unit 10, on shaft of the medical device (e.g., in the steerable portion, or at effector end 24).

Each of these interface elements is described hereinunder starting with dorsum interface 30.

Dorsum Interface

FIGS. 3*a*-*b* illustrate one embodiment of a dorsum interface 30 constructed in accordance with the teachings of the present invention. Dorsum interface 30 includes an arced shaped restraint 32 which is pivotally connected to the body of the palm interface 40 through hinge 31.

Hinge 31 may rotate freely or may be lockable and enables setting of an angle between handle 32 and palm interface distal end 42.

Element 33 serves as the elastic/deformable connection between dorsum interface and the back of the human hand (dorsum).

Dorsum interface 30 allows the user to control the spatial position and orientation of the device. When the user disengages from palm surface 42 and finger interface 60 as is shown in FIGS. 3*c*-*d*, element 33 of dorsum interface 30 enables the user to change the height, angle and rotation of a medical device attached to control unit 10 with respect to the tissue access site. Such control is achieved by hand movements around the elbow and shoulder joints and to a lesser degree by torso movements without a need to actually grasp the palm surface 42. Dorsum interface 30 also allows the user to release the finger hold on palm interface 40, thereby providing rest for the operating hand while still being engaged to interface 80.

Palm Interface

Palm interface 40 measures the orientation of a user's arm with respect to the device attached to control unit 10.

FIGS. 4*a*-*e* illustrate the main components of palm interface 40. Base 41 is the connection between housing 14 and palm surface 42. Base 41 serves as the housing for motor 49. Motor 49 controls the position of spherical brake 43. Inner spherical body 48 shown in FIG. 4*c* is fixed without moving to base 41 and contains joy stick sensor 50. Hemi-spherical parts 44 and 45 are connected to each other and contain inner spherical body 48 thus forming a ball joint/gimbal. Cylinder 51 connects rod 53 with top surface of part 45. When assembled, parts 44 and 45 can rotate around part 48 thereby rotating rod 53 of joy stick sensor 50. Pin 56 is connected to inner spherical body 48 and placed in slot 57. This configuration prevents parts 44 and 45 of the ball joint from undesired twist around a third axis of inner ball 48. Beam 47 connects the ball joint (formed from parts 44 and 45) and palm surface 42.

Palm surface 42 is shaped as a hemisphere and can include electrical switches for controlling desired functions of the medical device. Switch 53 serves as a panic button. If a user senses that the medical device is not functioning as desired, actuation of the panic button immediately arrests the motors and prevents any function of the medical device.

Switch 52 controls a brake mechanism within the ball joint which can be activated by the user to "freeze" articulation at a desired orientation. When switch 52 is actuated, a spherical brake 43 engages part 44 (FIG. 4*e*) to apply friction thereto and prevent it from rotating with respect to part 50.

A second actuation of switch 52 actuates motor 49 which moves brake 43 away from part 44 (FIG. 4*d*). Switch 52 can also be used to set various operation modes of control unit 10 as is further described hereinbelow with reference to FIG. 18.

Figure 4G:
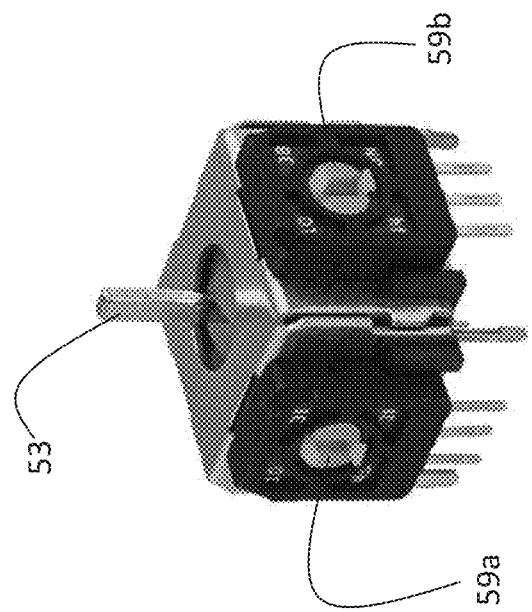
Figure 4F:
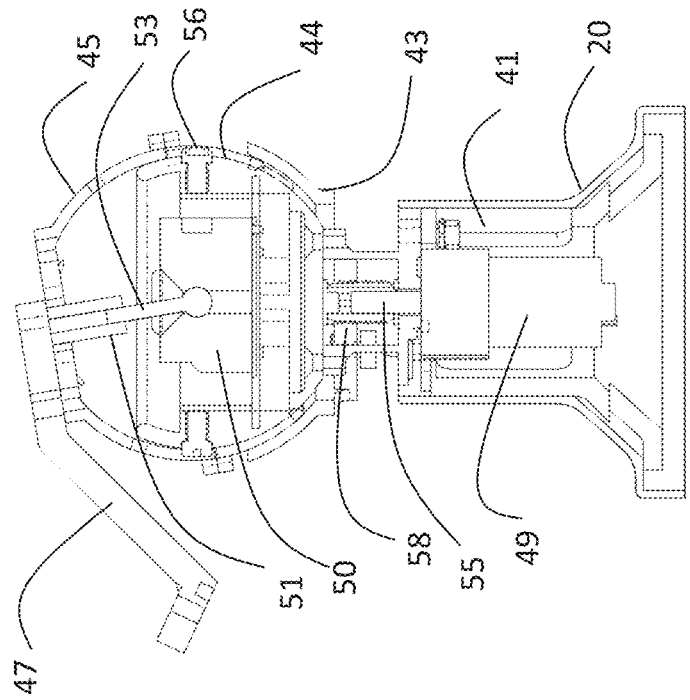

FIG. 4*f* is a cut-away view of palm interface 40. Motor 49 is connected to base 41. Nut 58 is fixed to axis 55 of motor 49 and is threaded to the base of brake 43; when axis 55 rotates, nut 58 rotates. Brake 43 is not able to rotate and translates the rotation of axis 55 to a linear movement. Rotation of axis 55 in a first direction moves brake 43 up and vice versa.

FIG. 4*g* illustrates a joy stick sensor which includes a central lever 53 that mechanically rotates 2 orthogonal potentiometers that measure the orientation of the lever at 2 orthogonal planes.

Figure 5B:
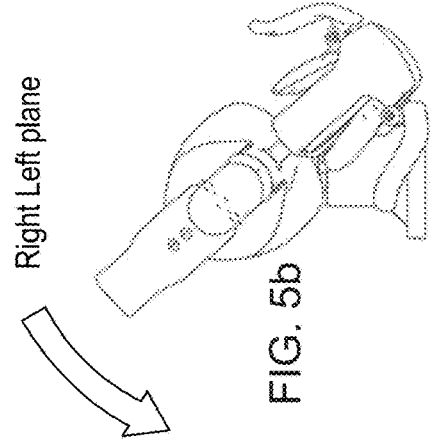
Figure 5D:
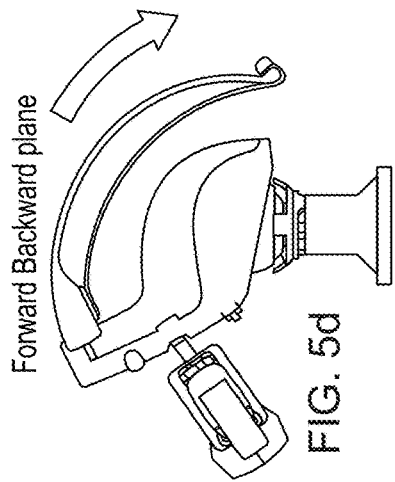
Figure 5A:
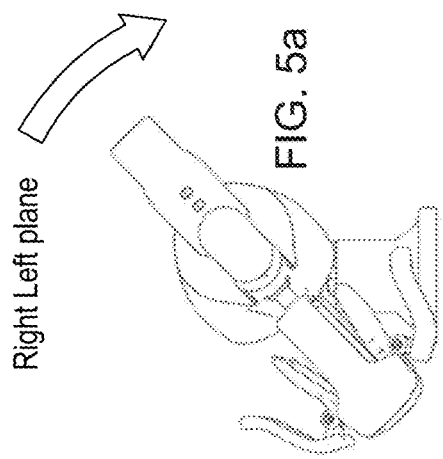

FIGS. 5*a*-*e* illustrate the relation between the orientation of the palm interface and the orientation of articulation 22. FIGS. 5*a*-*b* show palm interface 40 tilted on right-left plane resulting the articulation 22 to bend accordingly to side a and side b at first plane.

Figure 5C:
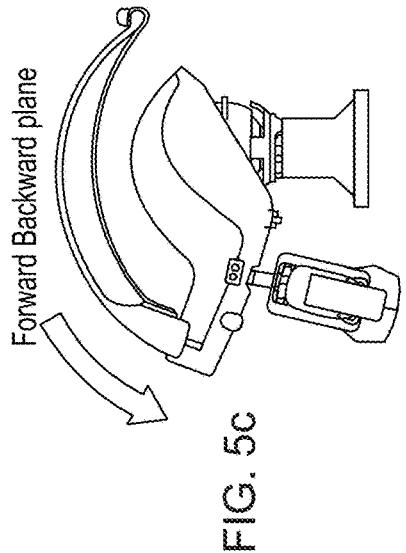

FIGS. 5*c*-*d* show palm interface 40 tilted on forward-backward plane resulting the articulation 22 to bend accordingly to side c and side d at a second plane orthogonal to the first plane. Orienting the palm interface in other planes will result equivalent orientation of the articulation.

Finger Interface

Finger interface 60 enables a user to control 2 main degrees of freedom of an effector end 24 (grasper): jaws open-close and the rotation of jaws. Such control is intuitive and can be effected simultaneously with palm interface 40 and dorsum interface 30.

FIGS. 6*a*-*b* illustrate finger interface 60 of control unit 10. FIG. 6*a* illustrates finger interface 60 connected to palm interface 40 via shaft 91. FIG. 6*b* illustrates ball joint mechanism 90 which includes shaft 91. Shaft 91 is capable of rotating with respect to housing 93. A nut 92 is used to regulate the force on the ball joint and allows the surgeon to fix shaft 91 at a desired orientation with respect to body 92. The distal end of shaft 91 is rectangular in shape in order to prevent finger interface 60 from rotating around shaft 91.

FIGS. 7*a*-*b* illustrate user options for ergonomic adjustments of finger interface 60. FIG. 7*a* illustrates the possible orientations of finger interface 60 with respect to palm surface 42. FIG. 7*b* illustrates adjustability of a distance between finger interface 60 and palm surface 42.

FIG. 8*a* illustrates housing 63 inner levers 61 and external levers 62 of finger interface 60; fingers (thumb, index) are postionable between inner levers 61 and external levers 62. Housing 63 is connected to shaft 91 via rectangle base 95 that prevents housing 63 from rotating around shaft 91.

Hinge 64 can be used to modify an angle between inner levers 61 and external; levers 62 in order to achieve an optimal fit with the users fingers.

Figure 8D:
Figure 8C:
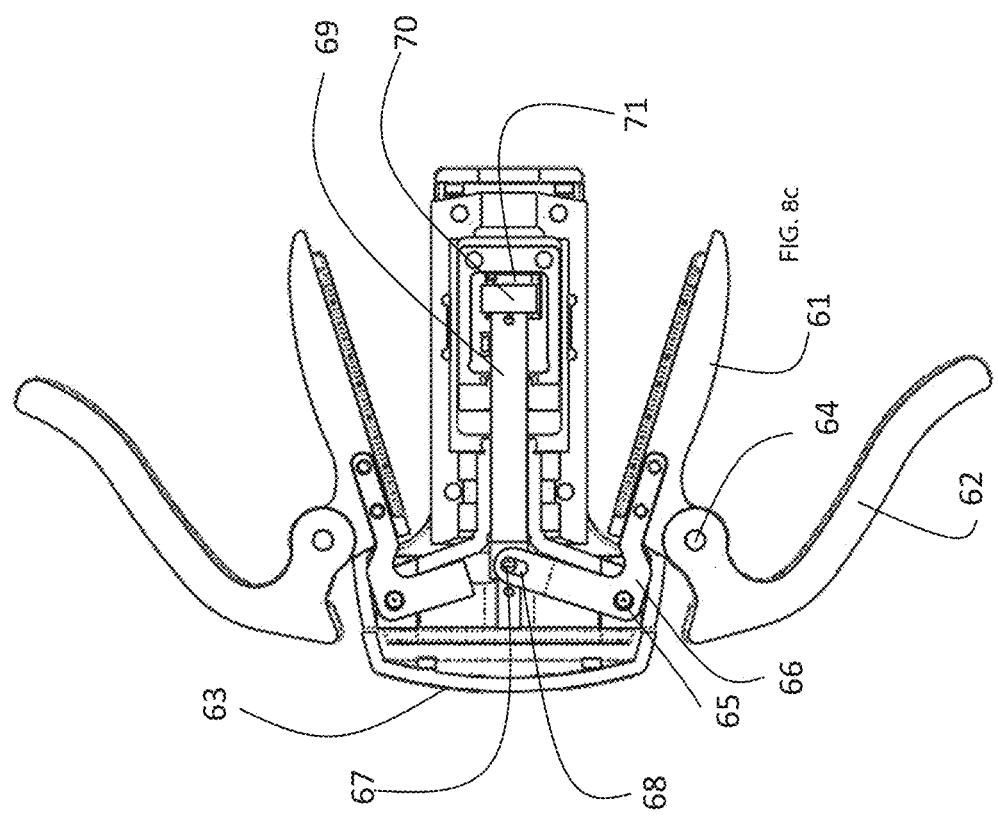
Figure 12C:
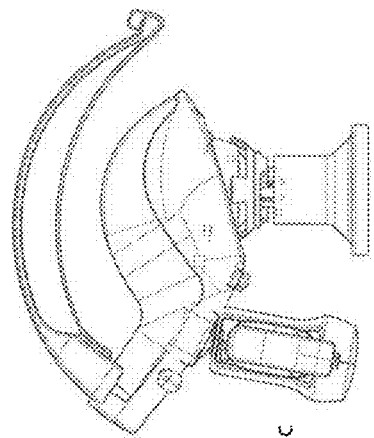
FIGS. 12a-e illustrate the operation of a second portion of the interface that controls a second steerable portion enabled by rotating the finger interface portion with respect to the palm interface portion of the present invention.
Figure 12E:
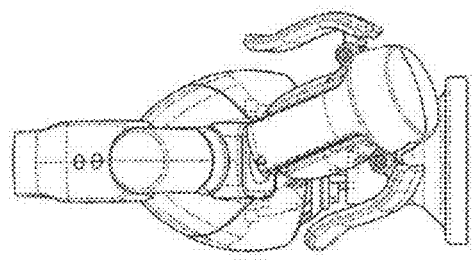
Figure 12B:
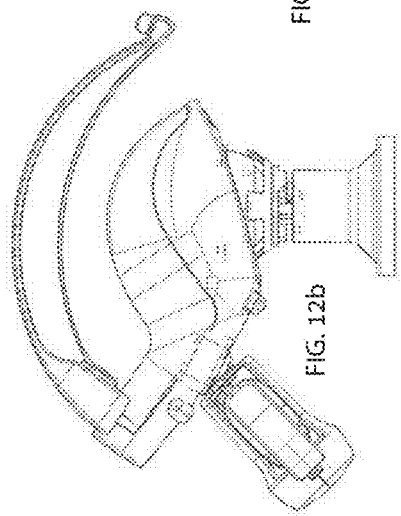
Figure 12D:
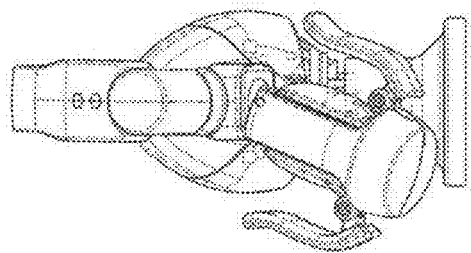
Figure 12A:
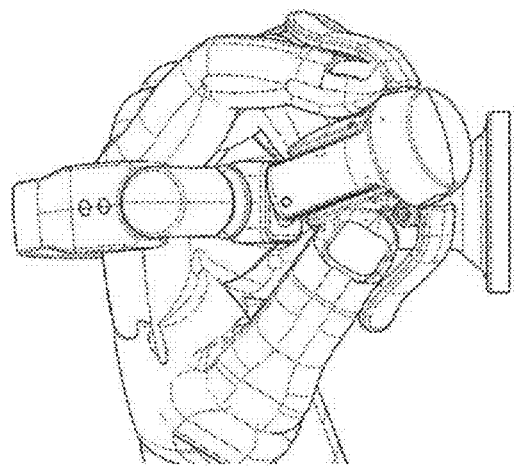
Figure 15:
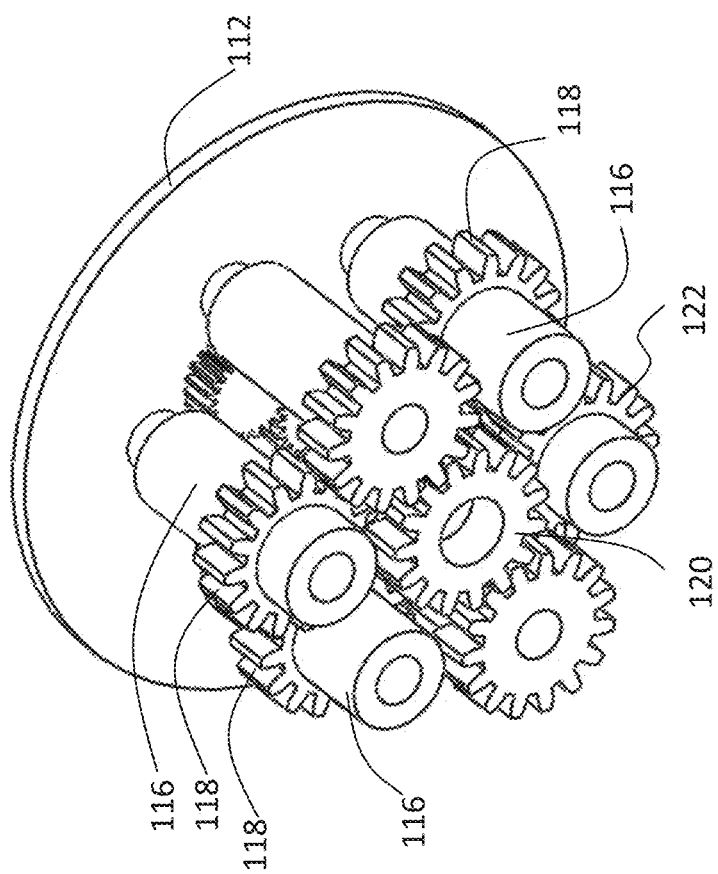

FIGS. 8*b*-*c* ire a cut-away view of finger interface 60. Inner levers 61 are fixed to brackets 66 which rotate around hinge 65. Pin 69 of central shaft 69 is positioned through elongated holes 67 at the end of brackets 66. Rotation of brackets 66 by inner levers 61 leads to linear movement of shaft 69 (through pin 67).

A magnet 70 is fixed to the end of shaft 69 and a magnetic sensor 71 (FIG. 8*d*) is positioned parallel to the main plane of shaft 69. Sensor 71 measures the linear movement of magnet 70. The measured movement is sampled by controller 15 and is used to control the open-close movement and position of the jaws.

FIG. 8*c* illustrates linear movement of magnet 70 resulting from rotation of inner levers 61 out of housing 63, when a user increases a distance between a thumb and index finger. Magnet 70 moves about 4 mm from an initial position in which inner levers 61 were pressed inward. External levers 62 can be used to open inner levers 61, or a spring (not shown) can be used in order to maintain inner levers 61 in a normally open position. The angle between inner levers 61 and external levers 62 can be adjusted using hinge 64.

FIGS. 9*a-i* illustrate jaws open-close modes of operation enabled by finger interface 60, corresponding linear travel of magnet 70 over magnetic sensor 71 and positions of the jaws of grasper 24.

FIGS. 10*a-c* illustrate rotation modes of the jaws and the mechanism for measuring the degree of rotation.

Magnet 70 (mounted on shaft 69) has a flat surface that fits within a D shaped opening 74 rotary position sensor 73. Shaft 69 slides through opening 74 when levers 61 and 62 are rotated by the user. Rotation of levers 61 and 62 rotates housing 79 and shaft 69 with respect to body 63 of finger interface 60. Rotary position sensor 73 is fixed to body 63, and as such shaft 69 can rotate inner body 75 of rotary position sensor 73 thus enabling measurement of an angle of rotation between levers 61 and 62 and shaft 91. Rotary position sensor 73 data is sampled by controller 15 which compares the orientation of finger interface 60 to the orientation of jaws of grasper 24. If there is a difference controller 15 sends a command to the motors to match orientation of jaws of grasper 24 to the orientation of the user's fingers.

FIGS. 11*a-b* illustrate an embodiment of user interface 80 which can be used to control at least two steerable portions. FIG. 11*a* is a cut-away view of interface 80 showing an additional sensor 50*b* which enables control of a second steerable portion of a medical device (laparoscope). FIG. 11*b* illustrates articulation of two independent steerable portions, a proximal steerable portion 102 and a distal steerable portion 103.

FIGS. 12*a-e* illustrate operation of a second steerable portion via a finger rotation mechanism of interface 60. The first steerable portion is controlled via palm interface 40 as described above.

FIGS. 13*a-h* illustrate the various modes of operation of interface 40 and finger rotation mechanism of interface 60 and the resultant independent deflection of the two steerable portions. FIG. 13*a* shows the interface at the "home" position. The two independent steerable portions are co-linear as shown in FIG. 13*b*. FIG. 13*c* illustrates actuation of interface 40 resulting in deflection of proximal steerable portion 102 only (FIG. 13*d*). Actuation of interface 60 and resultant deflection of distal steerable portion 103 only are shown in FIGS. 13*e-f* (respectively), while actuation of both interfaces and resulting deflection of both steerable portions are shown in FIGS. 13*g-h* (respectively).

FIGS. 14*a*-16 illustrate a motorized drive unit 16 embodiment of control unit 10. As is shown in FIG. 14*a*, drive unit 16 includes a motor pack 102 and a cable pulley system 104.

Motor pack 102 includes one or more motors 108 (three of five motors shown in FIG. 14*a*) which are individually actuated by interface 80. Motors 108 can be electric motors (e.g. FAULHABER motors 1024 with gear ratios of 1:256 1:64) powered by a battery pack (e.g. 3 AA 1.5V rechargeable batteries not shown) housed in proximal end 130. Motor pack 102 is positioned between a proximal end 130 of housing 14 and a motor housing floor 112.

In a preferred embodiment of the present invention, control unit 10 includes 5 motors 108, 3 motors for pulling and releasing control cables, one motor 108 for opening and closing the jaws of grasper 24 and one motor 108 for rotating the jaws.

Motors 108 that pull and release the control cables are arranged around a central longitudinal axis point of motor pack 102 offset at 120 degrees from each other. Such an arrangement allows simultaneous operation of three control cables enabling full control of an articulated joint.

As is shown in FIG. 14*a*, drive unit 16 also includes linkage 128 for actuating grasper 24. Linkage 128 is actuated by a motor 130 which drives a drive gear positioned within proximal end 130. The motor drive gear meshes with a second gear which is attached directly to a shaft of linkage 128 within proximal end 130.

Proximal end 130 can also include a memory unit and controller chip as well as ports for connecting control unit 10 to a computer to upload firmware, calibrate the operation of motors 108 and the interface elements.

Figure 16:
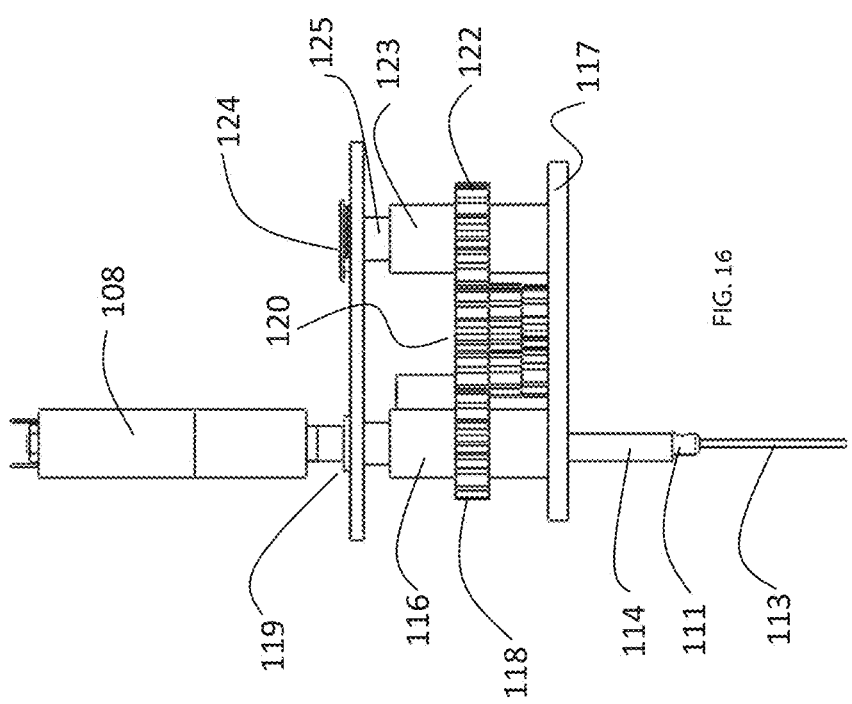

Motors 108 are connected to cable pullers 114 through screw housing 116 via a motor-screw coupling 119 (FIG. 16). Screw housing 116 functions in translating rotational movement of a drive shaft of motor 108 to a linear motion (up/down) of cable puller 114 (shown separately in FIG. 14*b*). Motor 108 rotates screw housing 116 that is coupled to the motor gear via motor-screw coupling 119 (FIG. 16). The proximal portion of cable puller 114 includes a spiral thread (Shown in FIG. 14*b*) that engages a spiral groove in screw housing 116. Cable puller 114 passes through a semi-circular opening in housing floor 117 which prevents it from rotating and thus forces it to move linearly (up/down) through the opening under rotation of motor 108. The distal portion of cable puller 114 includes a groove 111 (FIG. 14*b*) for coupling to a cable 113 (FIG. 16) attached to cable head 115.

Drive unit 16 also includes a gear cluster 106 (shown in isolated view in FIG. 15) which is positioned between motor pack 102 and cable pulley system 104. Gear cluster 106 includes drive gears 118 which are mounted around screw housings 116, and non-drive gears 130 which interconnect drive gears 118 with sensor housing gears 122.

FIG. 16 illustrates the drive relationship between drive gear 118, non-drive gear 130 and sensor housing gear 122.

Drive gear 118 rotates with rotation of motor 108 to rotate non-drive gear 130 which in turn rotates sensor housing gear 122. Sensor housing gear 122 rotates sensor housing 123 against a rotation sensor 124, this provides drive unit 16 with an indication of the extent of rotation and thus the extent of up/down movement of cable puller 114. Rotation sensor 124 can include a magnetic rotation chip which is located above a magnetic disk 125 which is fixed to housing 123. The chip can sense the rotation of magnetic disk 125 from a distance of up to 1 mm.

Control unit 10 can also include accelerometers and/or gyroscopes for sensing up/down and side-to-side movement of control unit 10, as well as angular rotation and velocity thereof. Such movement and angular parameters can be used to provide feedback to surgeon with respect to device positioning within the body cavity and/or limit the degree of interface actuation at certain angles of the device.

Figure 17:
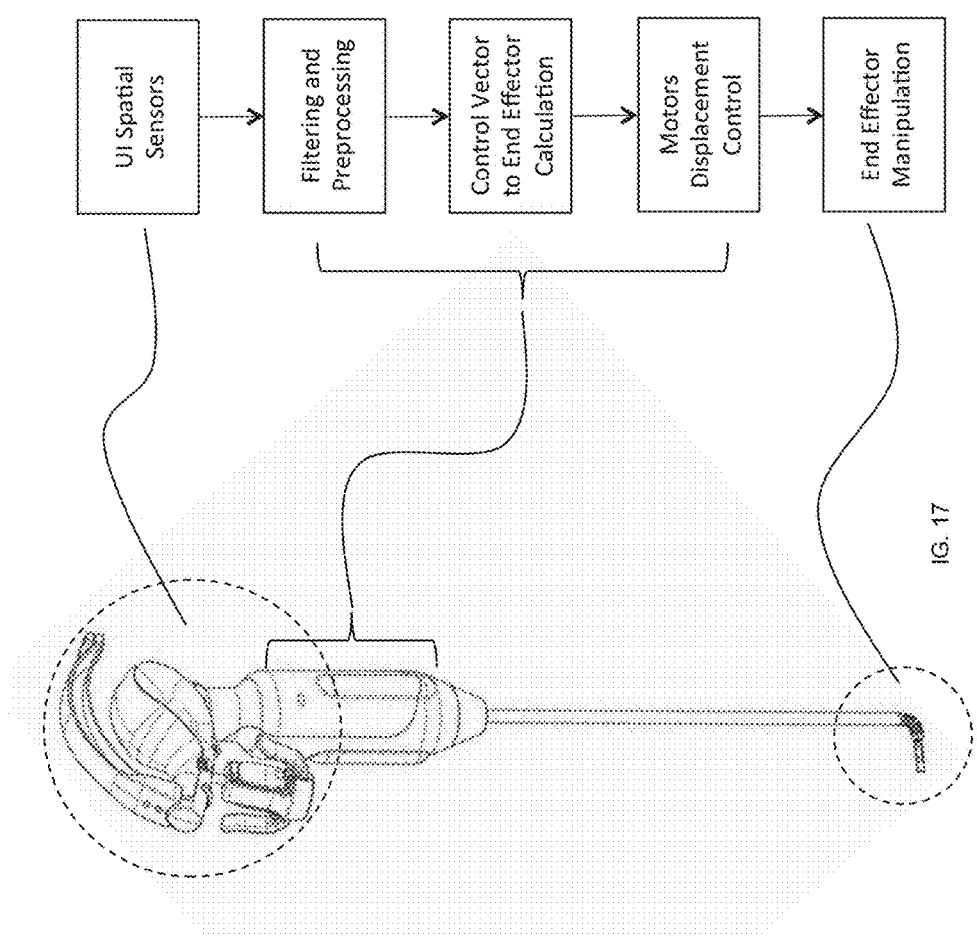
FIG. 17 illustrates how user interface (UI) movements translate into activation signals in control unit and movement of a laparoscopic tool attached thereto.

As is described hereinabove, operating a surgical tool attached to control unit 10 is effected by establishing a functional relationship between the orientation of palm interface 40 and direction of articulation movement of finger interface 60 and the action and movement (e.g. rotation) of the end effector. FIG. 17 illustrates the functional relationship between interface 80 (UI), control unit 10 and an attached laparoscope that enables a user to control a surgical tool via palm and finger movement.

Control unit 10 also enables other useful modes of operation. Such operating modes can be initiated via a control switch located at control unit 10, at a position reachable by a user's finger when the user's hand is placed in interface 80.

Activation and (deactivation) can be effected via a specific sequence/duration of click(s) on a control switch.

Figure 18:
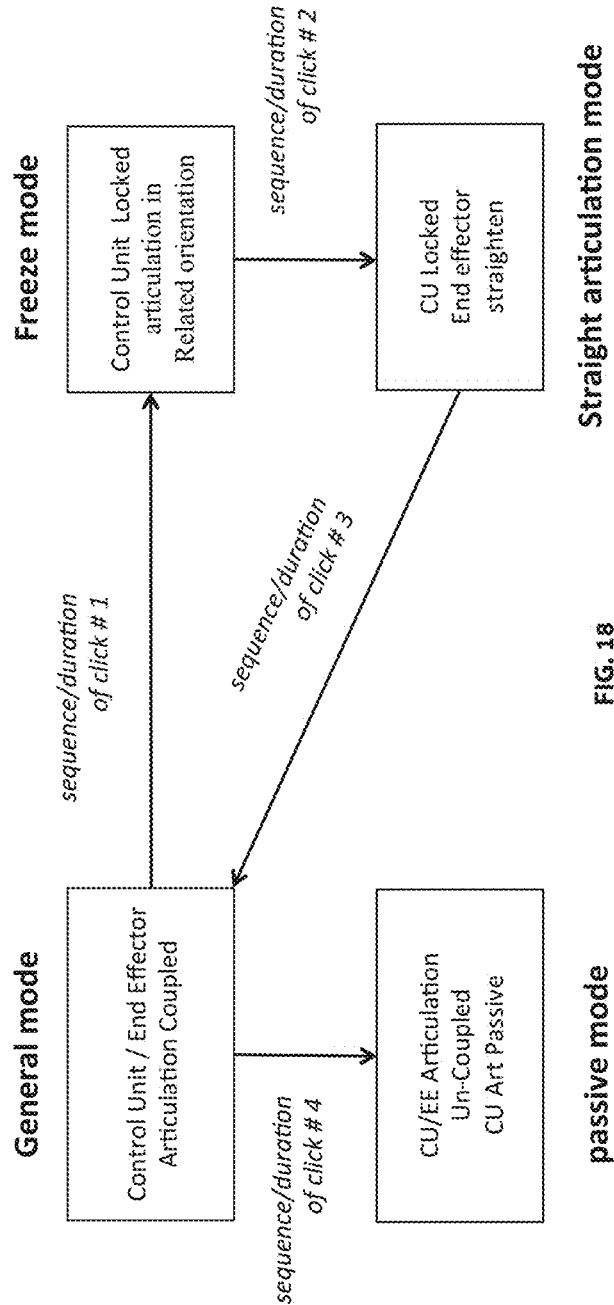
FIG. 18 illustrates various operational modes of the control unit of the present invention.

Several modes of operation, each activatable via a specific sequence/duration of clicks are illustrated in FIG. 18. Such modes can are facilitated via a braking mechanism of control unit 10 (motor 49 and spherical brake 43 shown in FIGS. 4*a*-*g* can be used as a braking mechanism).

For example, one specific sequence/duration of click(s) can activate a "freeze mode" (locking palm interface 40 and attached tool in a specific position) via motor 49 which moves the braking ring towards hemi-spherical part 44. Motor 49 is automatically deactivated when control unit 10 detects that sufficient breaking force is applied on hemi-spherical part 44 in order to stop the pivoting maneuvers of the palm interface.

Thus, such a "freeze mode" enables the user to lock palm interface 40 and attached tool in a specific orientation.

Another specific sequence/duration of click(s) can activate a passive mode. Such a mode enables the user to move the palm interface without moving the attached tool.

A "passive joint" mode enables the user to work with a preferred articulation orientation while being free to choose a comfortable hand orientation on palm interface 40.

Another specific sequence/duration of click(s) can activate a "straight articulation" mode which actuate the motors in order to bring the articulation to a straight orientation and then freezes the articulable shaft of the surgical tool in a straight orientation while allowing palm interface 40 to move freely.

A "straight articulation" mode is useful for advancing a tool through a trocar; in addition, when in a straight configuration, the tool can mimic traditional laparoscopic tools.

In any of the above modes, finger interface 60 is typically not effected, i.e. the user can use this interface to, for example, open/close and rotate the jaws of a grasper, however a scenario in which activation also locks finger interface 60 is also envisaged herein. For example when the surgeon wishes to apply constant force with the jaws or fix the jaws in a preferred angle to each other he can activate these modes by operating the finger levers in a specific sequence/duration of click(s).

As used herein the term "about" refers to ±10%.

Additional objects, advantages, and novel features of the present invention will become apparent to one ordinarily skilled in the art upon examination of the following examples, which are not intended to be limiting.

EXAMPLES

Reference is now made to the following example, which together with the above descriptions, illustrates the invention in a non limiting fashion.

While working with several types of laparoscopic tools, the present inventor realized that the tool interface is its Achilles heel. In order to hold and operate a free standing laparoscopic tools, one is required to perform unnatural movements with limited degree of control and operability. This is especially true in cases where laparoscope positioning and tool manipulation are effected via a single multi-purpose interface (e.g. the common scissor-like handles that are used for locating the laparoscope and actuating the tissue manipulating end). In order to overcome these deficiencies of prior art interfaces, the present inventor set out to devise an interface that separates the functions of a laparoscope into discrete interface elements and yet enables complete and simultaneous control over such interfaces via a single hand.

In reducing the present invention to practice, the present inventor experimented with several prototypes which implement the above interface design philosophy. The solution to the above problem turned out to be an interface that intuitively links the movement of the surgeons hand to that of the laparoscope and utilizes three distinct portions of the hand to operate three distinct interface elements.

Figure 19:
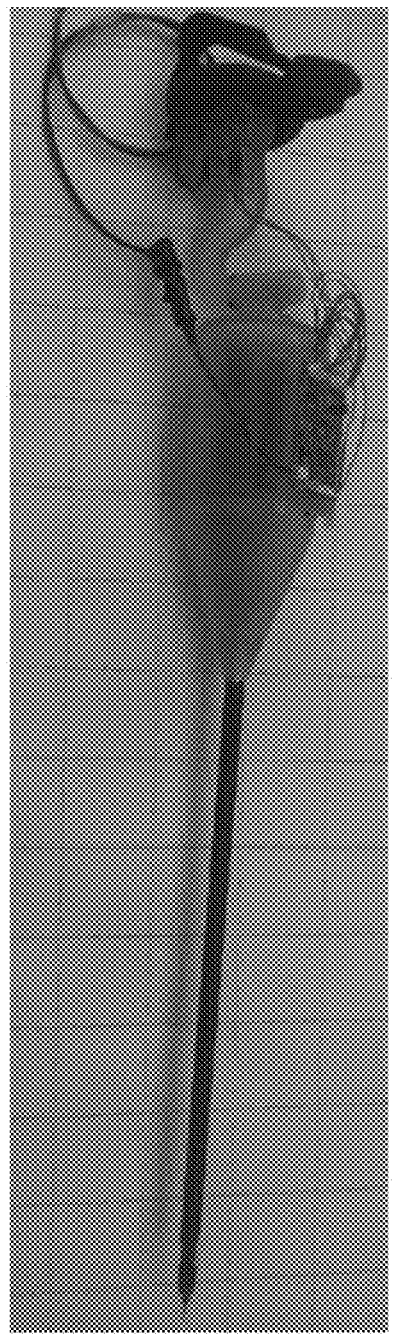
FIGS. 19-20 illustrate a prototype control unit constructed in accordance with the teachings of the present invention.
Figure 20:
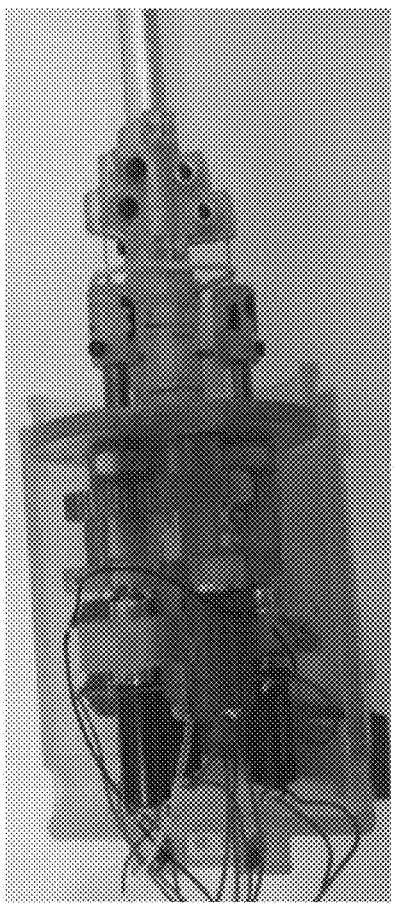

FIG. 19 illustrates a prototype control unit attached to a laparoscopic shaft. FIG. 20 illustrates the drive unit portion of the control unit.

This prototype includes a motor pack connected to the pulleys of the tool. The motor pack included small motors and transmissions that actuated the 4 degrees of freedom. The size and the weight of the motor pack were small enough to be carried by the surgeon. The interface was connected to the upper side of the motor pack in the same direction of the shaft axis. A joint between the motor pack and the interface allowed the surgeon to change the orientation between the interface and the long axis of the shaft. The motor pack included programmable control circuit that allowed the installing control software. While testing the tool the motor pack used batteries or cellphone Transformer.

Operability of the present control unit and interface was tested on a group of novice users using an attached laparoscopic phantom and standard laparoscope control tests. The users completed tasks such as grabbing small objects and moving them into small cups or threading small rubber loops on rods within minutes. The users were also capable of grabbing a surgical needle in the right orientation within minutes. A surgeon that tested the interface demonstrated a first complete suture 10 minutes after a short preliminary introduction to the interface.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A control unit for a medical device, the control unit comprising a user interface including
   (a) a first interface being mounted on a pivotal support attached to a housing of the control unit, said first interface being engageable by a palm of a hand and being operable to tilt forward-backward and right-left without requiring use of any fingers of said hand;
   (b) a restraint being pivotally attached to said first interface and having an element capable of elastically deforming to apply a restraining force to a back of said hand when said palm is engaged with said first interface, said element being for partially surrounding said hand; and (c) a second interface being pivotally attached to said first interface and being engageable by one or more fingers of said hand.

2. The control unit of claim 1, wherein said pivotal support is gimbaled.

3. The control unit of claim 1, wherein said housing includes a drive unit.

4. The control unit of claim 1, wherein said second interface includes levers simultaneously operable via thumb and index finger of said hand.

5. The control unit of claim 1, wherein said first interface can be tilted with respect to said pivotal support.

6. The control unit of claim 5, wherein tilting of said first interface deflects a steerable portion of the medical device.

7. The control unit of claim 4, wherein said levers operate an effector end of the medical device.

8. The control unit of claim 1, wherein said second interface can be tilted with respect to said first interface.

9. The control unit of claim 5, wherein tilting of said second interface deflects an effector end of the medical device.

10. A control unit for a minimally invasive surgical tool, the control unit comprising a user interface including:
 (a) a first interface control being for elastically deforming to apply a restraining force to a back of a hand of a user and being for controlling an angle and height of the minimally invasive surgical tool with respect to a tissue access site;
 (b) a second interface control being engageable by a palm of said hand of said user and being for controlling a deflection of a steerable portion of the minimally invasive surgical tool, said second interface being operable to tilt forward-backward and right-left without requiring use of any fingers of said hand; and
 (c) a third interface control being engageable by one or more fingers of said user and being for controlling a tissue manipulating end of the minimally invasive surgical tool.

11. The control unit of claim 10, wherein said second interface control is gimbaled.

12. The control unit of claim 10, wherein said first interface control includes an arm hingedly connected to a dorsum pad, said arm being configured for partially surrounding said hand.

13. The control unit of claim 1, further comprising a knob for rotating said housing of said control unit with respect to said first, second and third interface controls.

14. The control unit of claim 10, wherein said third interface control includes a pair of finger holds operable via a thumb and index finger.

15. The control unit of claim 10, wherein said third interface control includes a ball rotatable around at least two perpendicular axis.

16. The control unit of claim 10, wherein a user can simultaneously operate said first, second and third interface controls via a single hand.

17. The control unit of claim 10, wherein a functional linkage between said second or third interface and the minimally invasive surgical tool can be disengaged by a user.

18. The control unit of claim 17, further comprising a user engageable switch for activating/deactivating said functional linkage.

19. The control unit of claim 17, wherein deactivation of said functional linkage freezes the minimally invasive surgical tool in a preset position.

20. The control unit of claim 19, wherein said second or said third interface can be manipulated by a user when said minimally invasive surgical tool is frozen in position.

* * * * *